United States Patent [19]
Lok et al.

[11] Patent Number: 4,686,092
[45] Date of Patent: Aug. 11, 1987

[54] MANGANESE-ALUMINUM-PHOSPHORUS-SILICON-OXIDE MOLECULAR SIEVES

[75] Inventors: Brent M. T. Lok, New City; Bonita K. Marcus, Rye; Edith M. Flanigen, White Plains, all of N.Y.

[73] Assignee: Union Carbide Corporation, Danbury, Conn.

[21] Appl. No.: 600,175

[22] Filed: Apr. 13, 1984

[51] Int. Cl.$^4$ .................. C01B 25/26; B01J 27/18; B01J 27/182
[52] U.S. Cl. .................. 423/306; 502/214
[58] Field of Search .............. 423/305, 306, 326, 328, 423/329; 502/60, 62, 77, 162, 164, 208, 214

[56] References Cited

U.S. PATENT DOCUMENTS

| | | | |
|---|---|---|---|
| 4,310,440 | 1/1982 | Wilson et al. | 423/305 X |
| 4,420,467 | 12/1983 | Whittam | 423/328 |
| 4,440,871 | 4/1984 | Lok et al. | 502/214 |
| 4,486,397 | 12/1984 | Eshraghi et al. | 423/306 |
| 4,500,651 | 2/1985 | Lok et al. | 502/208 |
| 4,567,029 | 1/1986 | Wilson et al. | 423/306 |

FOREIGN PATENT DOCUMENTS

| | | |
|---|---|---|
| 0054364 | 6/1982 | European Pat. Off. . |
| 0055046 | 6/1982 | European Pat. Off. . |
| 0055529 | 7/1982 | European Pat. Off. . |
| 0059059 | 9/1982 | European Pat. Off. . |

OTHER PUBLICATIONS

Haggin, C & En, Jun. 20, 1983, pp. 36 & 37.

Primary Examiner—William R. Dixon, Jr.
Assistant Examiner—R. Bruce Breneman
Attorney, Agent, or Firm—Vincent J. Vasta, Jr.

[57] ABSTRACT

Crystalline molecular sieves having three-dimensional microporous framework structures of $MnO_2$, $AlO_2$, $SiO_2$ and $PO_2$ tetrahedral oxide units are disclosed. These molecular sieves have an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$; and "w", "x", "y" and "z" represent the mole fractions of manganese, aluminum, phosphorus and silicon, respectively, present as tetrahedral oxides. Their use as adsorbents, catalysts, etc. is also disclosed.

26 Claims, 3 Drawing Figures

MANGANESE-ALUMINUM-PHOSPHORUS-SILICON-OXIDE MOLECULAR SIEVES

FIELD OF THE INVENTION

The instant invention relates to a novel class of crystalline microporous molecular sieves, and to the method of their preparation. The invention relates to manganese-aluminum-phosphorus-silicon-oxide molecular sieves having manganese, aluminum, phosphorus and silicon in the form of framework tetrahedral oxides. These compositions may be prepared hydrothermally from gels containing reactive compounds of manganese, aluminum, phosphorus and silicon capable of forming framework tetrahedral oxides, and preferably at least one organic templating agent which functions in part to determine the course of the crystallization mechanism and the structure of the crystalline product.

BACKGROUND OF THE INVENTION

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6 Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed July 26, 1982, now U.S. Pat. No. 4,440,871, there is described a novel class of silicon-substituted aluminophosphates which are both microporous and crystalline. The materials have a three dimensional crystal framework of $PO_2^+$, $AlO_2^-$ and $SiO_2$ tetrahedral oxide units and, exclusive of any alkali metal or calcium which may optionally be present, an as-synthesized empirical chemical composition on an anhydrous basis of:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In copending and commonly assigned application Ser. No. 480,738, filed Mar. 31, 1983, now U.S. Pat. No. 4,500,651, there is described a novel class of titanium-containing molecular sieves whose chemical composition in the as-synthesized and anhydrous form is represented by the unit empirical formula:

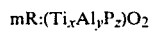

$$mR:(Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In copending and commonly assigned application Ser. No. 514,334, filed July 15, 1983 now U.S. Pat. No. 4,567,029, there is described a novel class of crystalline metal aluminophosphates having three-dimensional microporous framework structures of $MO_2$, $AlO_2$ and $PO_2$ tetrahedral units and having an empirical chemical composition on an anhydrous basis expressed by the formula:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; "x", "y" and "z" represent the mole fraction of the metal "M", aluminum and phosphorus, respectively, present as tetrahedral oxides.

In copending and commonly assigned application Ser. No. 514,335, filed July 15, 1983 now U.S. Pat. No. 4,554,143, there is described a novel class of crystalline ferroaluminophosphates having a three-dimensional microporous framework structure of $FeO_2$, $AlO_2$ and $PO_2$ tetrahedral units and having an empirical chemical composition on an anhydrous basis expressed by the formula

$$mR:(Fe_xAl_yP_z)O_2$$

wherein "R" represents at least one organic templating agent present in the intracrystalline pore system; "m" represents the moles of "R" present per mole of (Fe$_x$Al$_y$P$_z$)O$_2$ and has a value of from zero to 0.3; and "x", "y" and "z" represent the mole fraction of the iron, aluminum and phosphorus, respectively, present as tetrahedral oxides.

The instant invention relates to new molecular sieves comprising framework tetrahedral units of MnO$_2^{-2}$, AlO$_2^-$ and PO$_2^+$ and SiO$_2$.

SUMMARY OF THE INVENTION

The instant invention relates to a new class of molecular sieves having a three-dimensional microporous crystal framework structures of MnO$_2^{-2}$, AlO$_2^-$, PO$_2^+$ and SiO$_2$ tetrahedral oxide units. These new manganese-aluminum-phosphorus-silicon-oxide molecular sieves exhibit ion-exchange, adsorption and catalytic properties and, accordingly, find wide use as adsorbents and catalysts. The members of this novel class of compositions have crystal framework structures of MnO$_2^{-2}$, AlO$_2^-$, PO$_2^+$ and SO$_2$ tetrahedral oxide units and have an empirical chemical composition on an anhydrous basis expressed by the formula:

mR:(Mn$_w$Al$_x$P$_y$Si$_z$)O$_2$ wherein "R" represents at least one organic templating agent present in the intracrystalline pore system; "m" represents the molar amount of "R" present per mole of (Mn$_w$Al$_x$P$_y$Si$_z$)O$_2$ and has a value of zero to about 0.3; and "w", "x", "y" and "z" represent the mole fractions of manganese, aluminum, phosphorus and silicon, respectively, present as tetrahedral oxides. The instant molecular sieve compositions are characterized in several ways as distinct from heretofore known molecular sieves, including the aforementioned ternary compositions. The instant molecular sieves are characterized by the enhanced thermal stability of certain species and by the exisjtence of species heretofore unknown for binary and ternary molecular sieves.

The molecular sieves of the instant invention will be generally referred to by the acronym "MnAPSO" to designate a structure framework of MnO$_2^{-2}$, AlO$_2^-$, PO$_2^+$ and SiO$_2$ tetrahedral units. Actual class members will be identified as structural species by assigning a number to the species and, accordingly, are identified as "MnAPSO-i" wherein "i" is an integer. The given species designation is not intended to denote a similarity in structure to any other species denominated by a numbering system.

DETAILED DESCRIPTION OF THE INVENTION

The instant invention relates to a new class of molecular sieves having a three-dimensional microporous crystal framework structures of MnO$_2^{-2}$, AlO$_2^-$, PO$_2^+$ and SiO$_2$ tetrahedral oxide units. These new molecular sieves exhibit ion-exchange, adsorption and catalytic properties and, accordingly, find wide use as adsorbents and catalysts.

Figure 1:
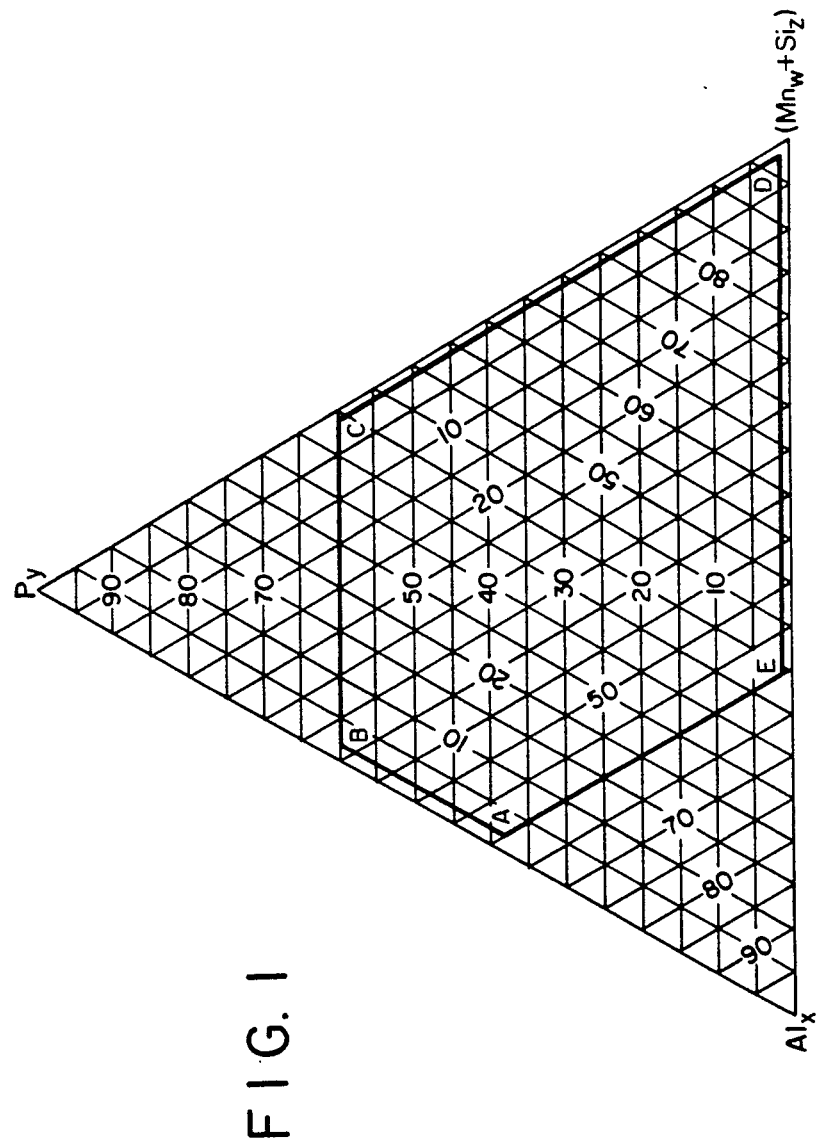
FIG. 1 is a ternary diagram wherein parameters relating to the instant compositions are set forth as mole fractions.

The MnAPSO molecular sieves of the instant invention have a framework structure of MnO$_2^{-2}$, AlO$_2^-$, PO$_2^+$, and SiO$_2$ tetrahedral units having an empirical chemical composition on an anhydrous basis expressed by the formula:

mR:(Mn$_w$Al$_x$P$_y$Si$_z$)O$_2$ wherein "R" represents at least one organic templating agent present in the intracrystalline pore system; "m" represents the molar amount of "R" present per mole of (Mn$_w$Al$_x$P$_y$Si$_z$)O$_2$ and has a value of zero to about 0.3; and "w", "x", "y" and "z" represent the mole fractions of element manganese, aluminum, phosphorus and silicon, respectively, present as tetrahedral oxides. The mole fractions "w", "x", "y" and "z" are generally defined as being within the pentagonal compositional area defined by points A, B, C, D and E of the ternary diagram of FIG. 1 and more preferably are generally defined as being within the tetragonal compositional area defined by points a, b, c and d of the ternary diagram of FIG. 2. Points A, B, C, D and E of FIG. 1 have the following values for "w", "x", "y", and "z":

| Point | Mole Fraction | | |
|---|---|---|---|
| | x | y | (w + z) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

Figure 2:
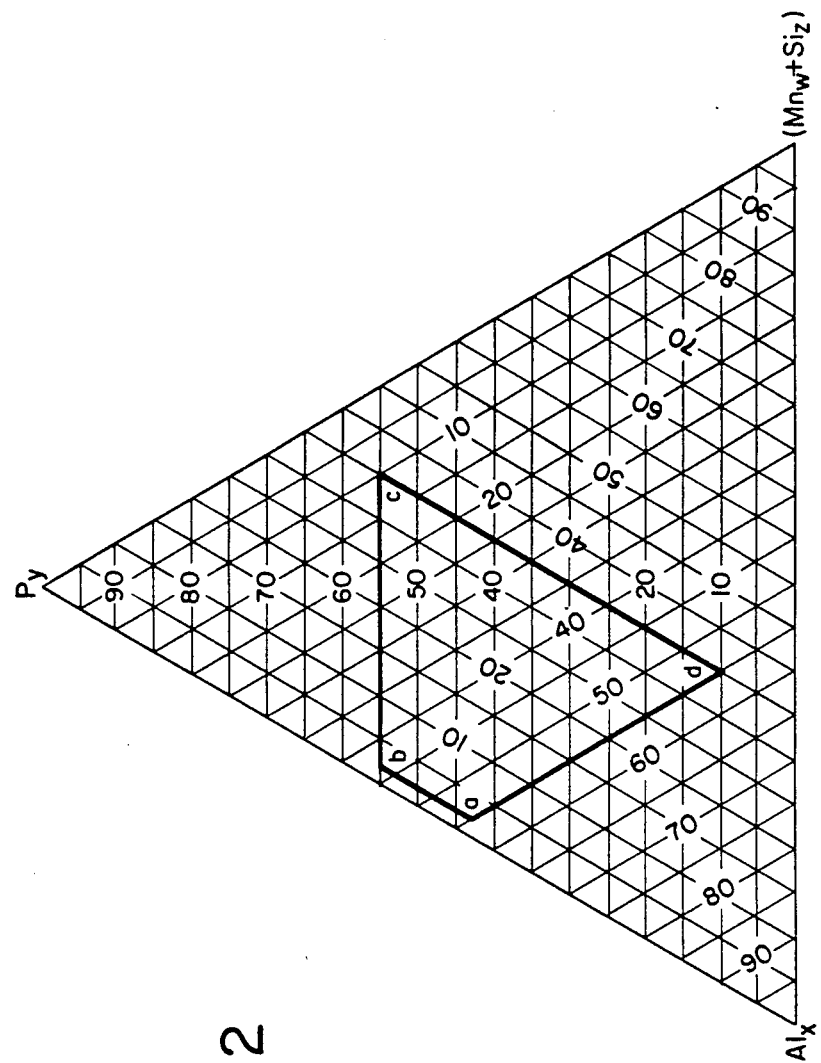
FIG. 2 is a ternary diagram wherein parameters relating to preferred compositions are set forth as mole fractions.

Points a, b, c, and d of FIG. 2 have the following values for "w", "x", "y", and "z":

| Point | Mole Fraction | | |
|---|---|---|---|
| | x | y | (w + z) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The MnAPSOs of this invention are useful as adsorbents, catalysts, ion-exchangers, and the like in much the same fashion as aluminosilicates have been employed heretofore, although their chemical and physical properties are not necessarily similar to those observed for aluminosilicates.

MnAPSO compositions are generally synthesized by hydrothermal crystallization from a reaction mixture containing reactive sources of manganese, silicon, aluminum and phosphorus, preferably an organic templating, i.e., structure-directing, agent, preferably a compound of an element or Group VA of the Periodic Table, and/or optionally an alkali or other metal. The reaction mixture is generally placed in a sealed pressure vessel, preferably lined with an inert plastic material such as polytetrafluoroethyl and heated, preferably under autogenous pressure at a temperature between about 50° C. and about 250° C., and preferably between about 100° C. and about 200° C. until crystals of the MnAPSO product are obtained, usually a period of from several hours to several weeks. Typical effective times of from 2 hours to about 30 days with generally from about 4 hours to about 20 days have been observed. The product is recovered by any convenient method such as centrifugation or filtration.

In synthesizing the MnAPSO compositions of the instant invention, it is preferred to employ a reaction mixture composition expressed in terms of the molar ratios as follows:

$$aR:(Mn_wAl_xP_ySi_z)O_2: bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "w", "x", "y" and "z" represent the mole fractions of manganese, aluminum, phosphorus and silicon, respectively, and each has a value of at least 0.01.

Figure 3:
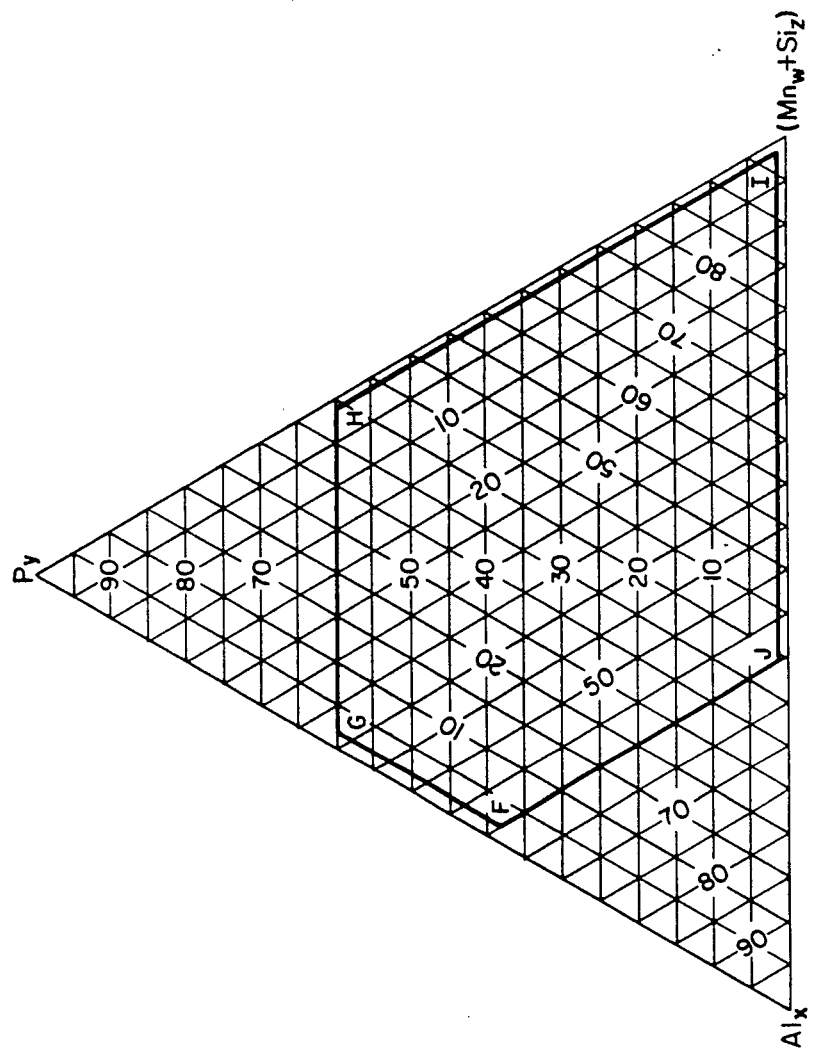
FIG. 3 is a ternary diagram wherein parameters relating to the reaction mixtures employed in the preparation of the compositions of this invention are set forth as mole fractions.

In a preferred embodiment the reaction mixture is selected such that the mole fractions "w", "x", "y" are generally defined as being within the pentagonal compositional area defined by points E, F, G, H and I of the ternary diagram of FIG. 3. Points E, F, G, H and I of FIG. 3 have the following values for "w", "x", "y" and "z":

| Point | Mole Fraction | | |
|---|---|---|---|
| | x | y | (w + z) |
| F | 0.60 | 0.38 | 0.02 |
| G | 0.38 | 0.60 | 0.02 |
| H | 0.01 | 0.60 | 0.39 |
| I | 0.01 | 0.01 | 0.98 |
| J | 0.60 | 0.01 | 0.39 |

For reasons unknown at present, not every reaction mixture gave crystalline MnAPSO products when reaction products were examined for MnAPSO products by X-ray analysis. Those reaction mixtures from which crystalline MnAPSO products were obtained are reported in the examples hereinafter as numbered examples. Those reaction mixtures from which MnAPSO products were not identified by use of X-ray analysis are also reported.

In the foregoing expression of the reaction composition, the reactants are normalized with respect to the total of "w", "x", "y" and "z" such that (w+x+y+z)=1.00 mole, whereas in the examples the reaction mixtures are expressed in terms of molar oxide ratios and may be normalized to the moles of P$_2$O$_5$. This latter form is readily converted to the former form by routine calculations by dividing the number of moles of each component (including the template and water) by the total number of moles of manganese, aluminum, phosphorus and silicon which results in normalized mole fractions based on total moles of the aforementioned components.

In forming reaction mixtures from which the instant molecular sieves are formed the organic templating agent can be any of those heretofore proposed for use in the synthetic of conventional zeolite aluminosilicates. In general these compounds contain elements of Group VA of the Periodic Table of Elements, particularly nitrogen, phosphorus, arsenic and antimony, preferably nitrogen or phosphorus and most preferably nitrogen, which compounds also contain at least one alkyl or aryl group having from 1 to 8 carbon atoms. Particularly preferred compounds for use as templating agents are the amines quatenary phosphonium and quaternary ammonium compounds, the latter two being represented generally by the formula R$_4$X$^+$ wherein "X" is nitrogen or phosphorous and each R is an alkyl or aryl group containing from 1 to 8 carbon atoms. Polymeric quaternary ammonium salts such as [(C$_{14}$H$_{32}$N$_2$)(OH)$_2$]$_x$ wherein "x" has a value of at least 2 are also suitably employed. The mono-, di- and triamines are advantageously utilized, either alone or in combination with a quaternary ammonium compound or other templating compound. Mixtures of two or more templating agents can either produce mixtures of the desired MnAPSOs or the more strongly directing templating species may control the course of the reaction with the other templating species serving primarily to establish the pH conditions of the reaction gel. Representative templating agents include: tetramethylammonium; tetraethylammonium; tetrapropylammonium; tetrabutylammonium ions; tetrapentylammonium ions; di-n-propylamine; tripropylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo(2,2,2)octane; N-methyldiethanolamine, N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; di-n-butylamine, neopentylamine; di-n-pentylamine; isopropylamine; t-butylamine; ethylenediamine; pyrrolidine; and 2-imidazolidone. Not every templating agent will direct the formation of every species of MnAPSO, i.e., a single templating agent can, with proper manipulation of the reaction conditions, direct the formation of several MnAPSO compositions, and a given MnAPSO composition can be produced using several different templating agents.

Most any reactive silicon source may be employed such that SiO$_2$ tetrahedral units are formed from a species present in situ. The reactive source of silicon may be silica, either as a silica sol or as fumed silica, a reactive solid amorphous precipitated silica, silica gel, alkoxides of silicon, silicic acid or alkali metal silicate and the like.

The reactive phosphorus source is phosphoric acid, but organic phosphates such as triethyl phosphate may be satisfactory, and so also may crystalline or amorphous aluminophosphates such as the AlPO$_4$ compositions of U.S. Pat. No. 4,310,440. Organo-phosphorus compounds, such as tetrabutylphosphonium bromide do not, apparently, serve as reactive sources of phosphorus, but these compounds may function as templating agents. Conventional phosphorus salts such as sodium metaphosphate, may be used, at least in part, as the phosphorus source, but are not preferred.

The preferred aluminum source is either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The source of manganese can be introduced into the reaction system in any form which permits the formation in situ of reactive form of manganese, i.e., reactive to form the framework tetrahedral unit of manganese. Compounds of manganese which may be employed herein include oxides, alkoxides, acetates, hydroxides, chlorides briomides, iodides, sulfates, nitrates, carboxylates and the like. For example, manganese acetate, manganese bromide, manganese sulfate, and the like are employable herein.

While not essential to the synthesis of MnAPSO compositions, stirring or other moderate agitation of the reaction mixture and/or seeding the reaction mixture with seed crystals of either the MnAPSO species to be produced or a topologically similar aluminophosphate, aluminosilicate or molecular sieve composition, facilitates the crystallization procedure.

After crystallization the MnAPSO product may be isolated and advantageously washed with water and dried in air. The as-synthesized MnAPSO generally contains within its internal pore system at least one form of the templating agent employed in its formation. Most commonly any organic moiety derived from any organic template is present, at least in part, as a charge-balancing cation as is generally the case with as-synthesized aluminosilicate zeolites prepared from organic-containing reaction systems. It is possible, however, that some or all of the organic moiety is an occluded molecular species in a particular MnAPSO species. As a general rule the templating agent, and hence the occluded organic species, is too large to move freely through the pore system of the MnAPSO product and must be removed by calcining the MnAPSO at temperatures of 200° C. to 700° C. to thermally degrade the organic species. In a few instances the pores of the MnAPSO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the MnAPSO phase wherein the organic moiety occupying the intracrystalline pore system as a result of the hydrothermal crystallization process has been reduced by post-synthesis treatment such that the value of "m" in the composition formula

$mR:(Mn_wAl_xP_ySi_z)O_2$ has a value of less than 0.02. The other symbols of the formula are as defined hereinabove. In those preparations in which an alkoxide is employed as the reactive source of manganese, aluminum, phosphorus or silicon, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized MnAPSO material.

Since the present MnAPSO compositions are formed from $MnO_2$, $AlO_2$, $PO_2$ and $SiO_2$ tetrahedral units which, respectively, have a net charge of $-2$, $-1$, $+1$ and 0. The matter of cation exchangeability is considerably more complicated than in the case of zeolitic molecular sieves in which, ideally, there is a stoichiometric relationship between $AlO_2^-$ tetrahedra and charge-balancing cations. In the instant compositions, an $AlO_2^-$ tetrahedron can be balanced electrically either by association with a $PO_2^-$ tetrahedron or a simple cation such as an alkali metal cation, a cation of manganese present in the reaction mixture, or an organic cation derived from the templating agent. Similarly an $MnO_2^{-2}$ tetrahedron can be balanced electrically by association with $PO_2^+$ tetrahedra, a cation of manganese, organic cations derived from the templating agent, a simple cation such as an alkali metal cation, or other divalent or polyvalent metal cations introduced from an extraneous source. It has also been postulated that non-adjacent $AlO_2^-$ and $PO_2^+$ tetrahedral pairs can be balanced by $Na^+$ and $OH^-$ respectively [Flanigen and Grose, Molecular Sieve Zeolites-I, ACS, Washington, DC (1971)]

The MnAPSO compositions of the present invention may exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of MnAPSO compositions is ordinarily possible only after the organic moiety present as a result of synthesis has been removed from the pore system. Dehydration to remove water present in the as-synthesized MnAPSO compositions can usually be accomplished, to some degree at least, in the usual manner without removal of the organic moiety, but the absence of the organic species greatly facilitates adsorption and desorption procedures. The MnAPSO materials will have various degrees of hydrothermal and thermal stability, some being quite remarkable in this regard, and will function as molecular sieve adsorbents and hydrocarbon conversion catalysts or catalyst bases.

The MnAPSOs are generally prepared using a stainless steel reaction vessel lined with the inert plastic material, polytetrafluoroethylene, to avoid contamination of the reaction mixture. In general, the final reaction mixture from which each MnAPSO composition is crystallized is prepared by forming mixtures of less than all of the reagents and thereafter incorporating into these mixtures additional reagents either singly or in the form of other intermediate mixtures of two or more reagents. In some instances the reagents admixed retain their identity in the intermediate mixture and in other cases some or all of the reagents are involved in chemical reactions to produce new reagents. The term "mixture" is applied in both cases. Further, unless otherwise specified, each intermediate mixture as well as the final reaction mixture was stirred until substantially homogeneous.

X-ray analysis of reaction products are obtained by X-ray analysis using standard X-ray powder diffraction techniques. The radiation source is a high-intensity, copper target, X-ray tube operated at 50 Kv and 40 ma. The diffraction pattern from the copper K-alpha radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as $2\theta$ where $\theta$ is the Bragg angle as observed on the strip chart. Intensities are determined from the heights of diffraction peaks after subtracting background, "$I_o$" being the intensity of the strongest line or peak, and "I" being the intensity of each of the other peaks. Alternatively, the X-ray patterns are obtained from the copper K-alpha radiation by use of computer based techniques using Siemens D-500 X-ray powder diffractometers, Siemens Type K-805 X-ray sources, available from Siemens Corporation, Cherry Hill, N.J., with appropriate computer interface.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their x-ray powder diffraction patterns and such may have one of the x-ray patterns set forth in the following Tables A through K, wherein said x-ray patterns are for both the as-synthesized and calcined forms unless otherwise noted:

TABLE A

| 2θ | d(Å) | Relative Intensity |
|---|---|---|
| | (MnAPSO-5) | |
| 7.3–7.7 | 12.11–11.48 | vs |
| 14.7–15.1 | 6.03–5.87 | m |
| 19.6–19.9 | 4.53–4.46 | m |
| 20.8–21.3 | 4.27–4.17 | m |
| 22.1–22.6 | 4.02–3.93 | m |
| 29.8–30.2 | 2.998–2.959 | m |

TABLE B

| 2θ | d(Å) | Relative Intensity |
|---|---|---|
| | (MnAPSO-11) | |
| 9.4–9.8 | 9.41–9.03 | m |
| 16.1–16.2 | 5.50–5.47 | vs-m |
| 21.0–21.5 | 4.23–4.13 | m-vs |
| 22.1–22.2 | 4.02–4.00 | m |
| 22.4–22.5 | 3.97–3.95 | m-s |
| 23.1–23.5 | 3.85–3.79 | m |

TABLE C

| 2θ | d(Å) | Relative Intensity |
|---|---|---|
| | (MnAPSO-16) | |
| 11.4–11.5 | 7.76–7.69 | m-vs |
| 18.6–18.7 | 4.77–4.75 | m |
| 21.9 | 4.06 | m-vs |
| 22.9–23.0 | 3.88–3.87 | w-m |
| 26.5–26.6 | 3.363–3.351 | m |
| 29.7–29.8 | 3.008–2.998 | m |

TABLE D

| 2θ | d(Å) | Relative Intensity |
|---|---|---|
| | (MnAPSO-20) | |
| 13.904–13.998 | 6.3692–6.3263 | m-vs |
| 19.723–19.818 | 4.5011–4.4918 | m |
| 24.223–24.329 | 3.6742–3.6584 | vs |
| 28.039–28.163 | 3.1822–3.1684 | w |
| 31.434–31.560 | 2.8458–2.8348 | w |
| 34.527–34.652 | 2.5976–2.5886 | w |

TABLE E

| 2θ | d(Å) | Relative Intensity |
|---|---|---|
| | (MnAPSO-31) | |
| 8.482–9.501 | 10.4240–9.3084 | m |
| 20.222–20.353 | 4.3913–4.3632 | m |
| 21.879–21.993 | 4.0622–4.0415 | m |
| 22.071–22.088 | 4.0272–4.0242 | m |
| 22.587–22.698 | 3.9364–3.9174 | vs |
| 31.724–31.836 | 2.8546–2.8108 | m |

TABLE F

| 2θ | d(Å) | Relative Intensity |
|---|---|---|
| | (MnAPSO-34) | |
| 9.4–9.6 | 9.41–9.21 | vs |
| 15.9–16.2 | 5.57–5.47 | m |
| 20.4–20.8 | 4.35–4.27 | m-vs |
| 25.0–25.3 | 3.562–3.520 | w-m |
| 31.0–31.3 | 2.885–2.858 | w-m |
| 33.6–33.9 | 2.667–2.644 | m |

TABLE G

| 2θ | d(Å) | Relative Intensity |
|---|---|---|
| | (MnAPSO-35) | |
| 10.8–11.0 | 8.19–8.04 | m-vs |
| 13.4–13.7 | 6.61–6.46 | m-s |
| 17.2–17.5 | 5.16–5.07 | m-s |
| 20.8–21.0 | 4.27–4.23 | m |
| 21.8–22.3 | 4.08–3.99 | m-vs |
| 28.2–28.7 | 3.164–3.110 | m |

TABLE H

| 2θ | d(Å) | Relative Intensity |
|---|---|---|
| | (MnAPSO-36) | |
| 7.596 | 11.6382 | m |
| 7.628–7.981 | 11.5899–11.0771 | vs |
| 8.105–8.299 | 10.9084–10.6537 | m |
| 16.395–16.673 | 5.4066–5.3172 | m |
| 19.052–19.414 | 4.6580–4.5721 | w |
| 20.744–20.871 | 4.2819–4.2560 | m |

TABLE J

| 2θ | d(Å) | Relative Intensity |
|---|---|---|
| | (MnAPSO-44) | |
| 9.420–9.498 | 9.3883–9.3110 | vs |
| 16.062–16.131 | 5.5179–5.4944 | m |
| 20.715–20.790 | 4.2877–4.2725 | s |
| 24.396–24.424 | 3.6485–3.6444 | m |
| 26.143–26.184 | 3.4085–3.4032 | m |
| 30.833–30.853 | 2.8999–2.8981 | m |

TABLE K

| 2θ | d(Å) | Relative Intensity |
|---|---|---|
| | (MnAPSO-47) | |
| 9.434–9.696 | 9.3746–9.1214 | vs |
| 15.946–16.276 | 5.5579–5.4457 | vw |
| 20.539–20.940 | 4.3242–4.2423 | vw-m |

TABLE K-continued

| 2θ | d(Å) | Relative Intensity |
|---|---|---|
| | (MnAPSO-47) | |
| 24.643 | 3.6125 | w |
| 30.511 | 2.9297 | w |
| 30.820–31.096 | 2.9011–2.8759 | vw |

PREPARATIVE REAGENTS

In the following examples the MnAPSO compositions were prepared using numerous reagents. The reagents employed and abbreviations employed herein, if any, for such reagents are as follows:

(a) Alipro: aluminum isopropoxide;
(b) CATAPAL; Trademark of Condea Corporation for hydrated pseudoboehomite
(c) LUDOX-LS: LUDOX-LS is the tradename of DuPont for an aqueous solution of b 30 weight percent $SiO_2$ and 0.1 weight percent $Na_2O$;
(d) $H_3PO_4$: 85 weight percent aqueous phosphoric acid;
(e) MnAc: Manganese acetate, $Mn(C_2H_3O_2)_2 \cdot 4H_2O$;
(f) TEAOH: 40 weight percent aqueous solution of tetraethylammonium hydroxide;
(g) TBAOH: 40 weight percent aqueous solution of tetrabutylammonium hydroxide;
(h) $Pr_2NH$: di-n-propylamine, $(C_3H_7)_2NH$;
(i) $Pr_3N$: trimpropylamine $(C_3H_7)_3N$;
(j) Quin: Quinuclidine, $(C_7H_{13}N)$;
(k) MQuin: Methyl Quinuclidine hydroxide, $(C_7H_{13}NCH_3OH)$;
(l) C-hex: cyclohexylamine;
(m) TMAOH: tetramethylammonium hydroxide;
(n) TPAOH: tetrapropylammonium hydroxide; and
(o) DEEA: 2-diethylaminoethanol.

PREPARATIVE PROCEDURES

The following preparative examples were carried out by forming a starting reaction mixture by adding the $H_3PO_4$ to one half the quantity of water. This mixture was mixed and to this mixture the aluminum isopropoxide or CATAPAL was added. This mixture was then blended until a homogeneous mixture was observed. To this mixture the LUDOX LS was added and the resulting mixture blended (about 2 minutes) until a homogeneous mixture was observed. A second mixture was prepared using the manganese acetate and the remainder (about 50%) of the water. The two mixtures were admixed and the resulting mixture blended until a homogeneous mixture was observed. The organic templating agent was then added to the resulting mixture and the resulting mixture blended until a homogeneous mixture was observed, i.e., about 2 to 4 minutes. (The pH of the mixture was measured and adjusted for temperature). The mixture was then placed in a lined (polytetrafluoroethylene) stainless steel pressure vessel and digested at a temperature (150° C. or 200° C.) for a time or placed in lined screw top bottles for digestion at 100° C. All digestions were carried out at the autogeneous pressure.

The molar composition for each preparation will be given by the relative moles of the components of the reaction mixture. $H_3PO_4$ and MnAc are given respectively in terms of $P_2O_5$ and MnO content of the reaction mixture.

The following examples are provided to further illustrate the invention and are not intended to be limiting thereof:

EXAMPLES 1 TO 64

MnAPSO molecular sieves were prepared according to the above identified procedure and the MnAPSO products determined by X-ray analysis. The results of examples 1 to 64 are set forth in Tables I to IV.

TABLE I

| Example[1] | Template | Temp (°C.) | Time (days) | MnAPSO Product[2] |
|---|---|---|---|---|
| 1 | TEAOH | 150 | 4 | MnAPSO-34; MnAPSO-5 |
| 2 | TEAOH | 150 | 11 | MnAPSO-5; MnAPSO-34 |
| 3 | TEAOH | 200 | 4 | MnAPSO-5; MnAPSO-34 |
| 4 | TEAOH | 200 | 11 | MnAPSO-5; MnAPSO-34 |
| 5 | TEAOH | 100 | 2 | —[3] |
| 6 | TEAOH | 100 | 7 | MnAPSO-34 |
| 7 | TEAOH | 150 | 2 | MnAPSO-34; MnAPSO-5 |
| 8 | TEAOH | 150 | 7 | MnAPSO-34; MnAPSO-5 |
| 9 | TEAOH | 200 | 2 | MnAPSO-5; MnAPSO-34 |
| 10 | TEAOH | 200 | 7 | MnAPSO-5; MnAPSO-34 |
| 11 | TEAOH | 100 | 14 | MnAPSO-34; |
| 12 | TEAOH | 150 | 14 | MnAPSO-34; MnAPSO-5 |
| 13 | TEAOH | 200 | 14 | MnAPSO-5; MnAPSO-34 |

[1]The reaction mixture comprised: 1.0 TEAOH: 0.2 MnO: 0.9 $Al_2O_3$: 0.9 $P_2O_5$: $rSiO_2$: 50 $H_2O$ where "r" was 0.2 for examples 1 to 4 and was 0.6 for examples 5 to 13.
[2]Major species as identified by x-ray powder diffraction pattern of product, except that when two species where identified the first species listed is the predominant species observed.
[3]No MnAPSO products were observed by x-ray analysis.

TABLE II

| Example[1] | Template | Temp (°C.) | Time (days) | MnAPSO Product[2] |
|---|---|---|---|---|
| 14 | Quin | 150 | 4 | MnAPSO-16; MnAPSO-35 |
| 15 | Quin | 150 | 11 | MnAPSO-16; MnAPSO-35 |
| 16 | Quin | 200 | 4 | MnAPSO-16; MnAPSO-35 |
| 17 | Quin | 200 | 11 | MnAPSO-16; MnAPSO-35 |
| 18 | Quin | 100 | 4 | MnAPSO-35 |
| 19 | Quin | 100 | 11 | MnAPSO-35 |
| 20 | MQuin | 150 | 2 | MnAPSO-35; MnAPSO-16 |
| 21 | MQuin | 150 | 7 | MnAPSO-35 |
| 22 | MQuin | 200 | 2 | MnAPSO-35 |
| 23 | MQuin | 200 | 7 | MnAPSO-35 |
| 24 | $Pr_2NH$ | 150 | 4 | MnAPSO-11 |
| 25 | $Pr_2NH$ | 150 | 11 | MnAPSO-11 |
| 26 | $Pr_2NH$ | 200 | 4 | MnAPSO-11; MnAPSO-39 |
| 27 | $Pr_2NH$ | 200 | 11 | MnAPSO-11; MnAPSO-39 |
| 28 | $Pr_2NH$ | 100 | 4 | —[3] |
| 29 | $Pr_2NH$ | 100 | 11 | —[3] |

[1]The reaction mixture comprised: 1.0 R: 0.2 MnO: 0.9 $Al_2O_3$: 0.9 $P_2O_5$: 0.2 $SiO_2$: 50 $H_2O$ where "R" is the template, as identified in Table II
[2]Major species as identified by x-ray powder diffraction pattern of product, except that when two species where identified the first species listed is the predominant species observed.
[3]No MnAPSO products were observed by x-ray analysis.

TABLE III

| Example[1] | Template | Temp (°C.) | Time (days) | MnAPSO Product[2] |
|---|---|---|---|---|
| 30 | $Pr_3N$ | 150 | 4 | MnAPSO-5 |
| 31 | $Pr_3N$ | 150 | 11 | MnAPSO-5 |
| 32 | $Pr_3N$ | 200 | 4 | MnAPSO-5 |
| 33 | $Pr_3N$ | 200 | 11 | MnAPSO-5 |
| 34 | $Pr_3N$ | 100 | 4 | —[3] |
| 35 | $Pr_3N$ | 100 | 11 | —[3] |
| 36 | TBAOH | 150 | 4 | —[3] |
| 37 | TBAOH | 150 | 10 | —[3] |
| 38 | TBAOH | 200 | 4 | MnAPSO-5 |
| 39 | TBAOH | 200 | 10 | MnAPSO-5 |
| 40 | C-hex | 150 | 3 | MnAPSO-13 |
| 41 | C-hex | 150 | 9 | MnAPSO-44; MnAPSO-13 |
| 42 | C-hex | 200 | 3 | MnAPSO-5; MnAPSO-44 |

TABLE III-continued

| Example[1] | Template | Temp (°C.) | Time (days) | MnAPSO Product[2] |
|---|---|---|---|---|
| 43 | C-hex | 200 | 9 | MnAPSO-5; MnAPSO-44 |

[1]The reaction mixture comprised:
(a) Examples 30 to 35: 1.0 Pr₃N; 0.2 MnO; 0.9 Al₂O₃; 0.9 P₂O₅; 0.2 SiO₂; 50 H₂O
(b) Examples 36 to 39: 2.0 TBAOH; 0.4 MnO; 0.8 Al₂O₃; 1.0 P₂O₅; 0.4 SiO₂; 50 H₂O
(c) Examples 40 to 43: 1.0 C-hex; 0.2 MnO; 0.9 Al₂O₃; 0.9 P₂O₅; 0.6 SiO₂; 50 H₂O
[2]Major species as identified by x-ray powder diffraction pattern of product, except that when two species where identified the first species listed is the predominant species observed.
[3]No MnAPSO products were observed by x-ray analysis.

TABLE IV

| Example[1] | Template | Temp (°C.) | Time (days) | MnAPSO Product[2] |
|---|---|---|---|---|
| 44 | TPAOH | 150 | 2 | MnAPSO-5 |
| 45 | TPAOH | 200 | 2 | MnAPSO-5 |
| 46 | TMAOH | 150 | 4 | MnAPSO-20 |
| 47 | TMAOH | 200 | 4 | MnAPSO-20 |
| 48 | DEA | 150 | 9 | MnAPSO-47 |
| 49 | DEA | 150 | 18 | MnAPSO-47 |
| 50[4] | Pr₂NH | 150 | 4 | MnAPSO-31 |
| 51[4] | Pr₂NH | 150 | 10 | MnAPSO-31; MnAPSO-46 |
| 52[4] | Pr₂NH | 200 | 4 | MnAPSO-31; MnAPSO-11 |
| 53[4] | Pr₂NH | 200 | 10 | MnAPSO-31; MnAPSO-11 |
| 54[4] | Pr₂NH | 150 | 2 | MnAPSO-31 |
| 55[4] | Pr₂NH | 150 | 2 | MnAPSO-31 |
| 56[4] | Pr₂NH | 200 | 2 | MnAPSO-31; MnAPSO-11 |
| 57 | Pr₂NH | 200 | 25 | MnAPSO-11; MnAPSO-5; MnAPSO-39; MnAPSO-46 |
| 58 | Quin | 225 | 5 | MnAPSO-16; MnAPSO-35 |
| 59[5] | Pr₃N | 150 | 2 | MnAPSO-36 |
| 60[5] | Pr₃N | 150 | 7 | MnAPSO-36; MnAPSO-5 |
| 61[5] | Pr₃N | 200 | 2 | MnAPSO-36; MnAPSO-5 |
| 62[5] | Pr₃N | 200 | 7 | MnAPSO-36; MnAPSO-5 |
| 63 | C-hex | 225 | 5 | MnAPSO-5; MnAPSO-44 |
| 64 | C-hex | 200 | 4 | MnAPSO-44 |

[1]The reaction mixtures comprised: 1.0 R; 0.2 MnO: 0.9 Al₂O₃; 0.9 P₂O₅; 0.6 SiO₂; 50 H₂O where R is as above identified and except than in examples 48, 49, 57, and 64 the moles of "R" was 2.0 and inexample 58 the coefficient for P₂O₅ was 1.0 instead of 0.9.
[2]Major species as identified by x-ray powder diffraction pattern of product, except that when two species where identified the first species listed is the predominant species observed.
[3]No MnAPSO products were observed by x-ray analysis.
[4]Seed crystals of AlPO₄-31 were employed (U.S. Pat. No. 4,310,440).
[5]Seed crystals of MnAPO-36 were employed, as disclosed in U.S. Serial No. 514,334, filed July 15, 1983.

EXAMPLE 65

(a) Samples of the MnAPSO products were calcined in air or nitrogen to remove at least part of the organic templating agent of the product. The example in which a given MnAPSO product was prepared is given in parenthesis. The adsorption capacities of each calcined sample were measured using a standard McBain-Bakr gravimetric adsorption apparatus. The samples were activated in a vacuum (less than 0.04 torr) at 350° C. prior to measurement. The McBain-Bakr data for the aforementioned MnAPSO molecular sieves are set forth hereinafter:

(a) MnAPSO-5 (Example 31):

| Adsorbate | Kinetic Diameter, Å | Pressure (Torr) | Temp (°C.) | Wt. % Adsorbed* |
|---|---|---|---|---|
| $O_2$ | 3.46 | 102 | −183 | 8.9 |
| $O_2$ | 3.46 | 750 | −183 | 10.8 |
| n-butane | 4.3 | 504 | 23.0 | 4.4 |
| cyclohexane | 6.0 | 65 | 23.4 | 5.4 |
| $H_2O$ | 2.65 | 4.6 | 23.0 | 8.1 |
| $H_2O$ | 2.65 | 19.5 | 23.0 | 17.1 |

*MnAPSO—5 was calcined at 600° C. in air for 4 hours.

The above data demonstrate that the pore size of the calcined MnAPSO-5 product is greater than 6.2 Å.

(b) MnAPSO-11 (Example 24):

| Adsorbate | Kinetic Diameter, Å | Pressure (Torr) | Temp (°C.) | Wt. % Adsorbed* |
|---|---|---|---|---|
| $O_2$ | 3.46 | 106 | −183 | 7.0 |
| $O_2$ | 3.46 | 744 | −183 | 11.1 |
| neopentane | 6.2 | 741 | 25.3 | 2.5 |
| isobutane | 5.0 | 740 | 24.2 | 3.5 |
| cyclohexane | 6.0 | 82 | 23.9 | 10.7 |
| $H_2O$ | 2.65 | 4.6 | 24.9 | 5.1 |
| $H_2O$ | 2.65 | 19 | 24.8 | 14.9 |

*MnAPSO was calcined at 600° in air for 2 hours.

The above data demonstrate that the pore size of the calcined MnAPSO-11 product is about 6.0 Å.

(c) MnAPSO-20 (Example 46):

| Adsorbate | Kinetic Diameter, Å | Pressure (Torr) | Temp (°C.) | Wt. % Adsorbed* |
|---|---|---|---|---|
| $O_2$ | 3.46 | 102 | −183 | 0.7 |
| $O_2$ | 3.46 | 744 | −183 | 1.2 |
| $H_2O$ | 2.65 | 4.6 | 23.3 | 9.0 |
| $H_2O$ | 2.65 | 19 | 23.2 | 13.7 |

*MnAPSO calcined at 500° C. in air for 1 hour.

The above data demonstrate that the pore size of the calcined MnAPSO-20 product is greater than about 2.65 Å and less than about 3.46 Å.

(d) MnAPSO-31 (Example 55):

| Adsorbate | Kinetic Diameter, Å | Pressure (Torr) | Temp (°C.) | Wt. % Adsorbed* |
|---|---|---|---|---|
| $O_2$ | 3.46 | 105 | −183 | 5.6 |
| $O_2$ | 3.46 | 741 | −183 | 9.7 |
| Neopentane | 6.2 | 739 | 23.5 | 4.6 |
| $H_2O$ | 2.65 | 4.6 | 23.8 | 5.8 |
| $H_2O$ | 2.65 | 20 | 24.0 | 15.5 |

*MnAPSO—31 calcined at 500° C. in air for 1.5 hours.

The above data demonstrate that the pore size of the calcined MnAPSO-31 product is greater than about 6.2 Å.

(e) MnAPSO-34 (Example 11):

| Adsorbate | Kinetic Diameter, Å | Pressure (Torr) | Temp (°C.) | Wt. % Adsorbed* |
|---|---|---|---|---|
| $O_2$ | 3.46 | 103 | −183 | 11.4 |
| $O_2$ | 3.46 | 731 | −183 | 15.6 |
| isobutane | 5.0 | 741 | 24.5 | 0.8 |
| n-hexane | 4.3 | 103 | 24.4 | 4.6 |
| $H_2O$ | 2.65 | 4.6 | 24.4 | 15.2 |
| $H_2O$ | 2.65 | 18.5 | 23.9 | 24.4 |

*MnAPSO—34 was calcined at 425° C. in nitrogen for 2 hours.

The above data demonstrate that the pore size of the calcined MnAPSO-34 product is about 4.3 Å.

(f) MnAPSO-35 (Example 21):

| Adsorbate | Kinetic Diameter, Å | Pressure (Torr) | Temp (°C.) | Wt. % Adsorbed* |
|---|---|---|---|---|
| $O_2$ | 3.46 | 103 | −183 | 1.8 |
| $O_2$ | 3.46 | 731 | −183 | 2.6 |
| n-hexane | 4.3 | 103 | 24.4 | 0.8 |
| $H_2O$ | 2.65 | 4.6 | 24.4 | 9.9 |

| Adsorbate | Kinetic Diameter, Å | Pressure (Torr) | Temp (°C.) | Wt. % Adsorbed* |
|---|---|---|---|---|
| H$_2$O | 2.65 | 18.5 | 23.9 | 15.9 |

*MnAPSO—35 was calcined at 500° C. in nitrogen for 2 hours.

The above data demonstrate that the pore size of the calcined MnAPSO-35 product is about 4.3 Å.

(g) MnAPSO-44 (Example 64):

| Adsorbate | Kinetic Diameter, Å | Pressure (Torr) | Temp (°C.) | Wt. % Adsorbed* |
|---|---|---|---|---|
| O$_2$ | 3.46 | 102 | −183 | 18.2 |
| O$_2$ | 3.46 | 744 | −183 | 20.1 |
| n-hexane | 4.3 | 95 | 23.6 | 1.3 |
| isobutane | 5.0 | 746 | 24.1 | 0.5 |
| H$_2$O | 2.65 | 4.6 | 24.8 | 22.7 |
| H$_2$O | 2.65 | 19 | 29.8 | 27.7 |

*MnAPSO—44 was calcined at 500° C. in air for 1.0 hour.

The above data demonstrate that the pore size of the calcined MnAPSO-44 product about 4.3 Å.

EXAMPLE 66

Samples of the as-synthesized products of certain examples were subjected to chemical analysis. The example in which a given MnAPSO was prepared is noted in parenthesis. The chemical analysis for these MnAPSOs was as follows:

(a) The chemical analysis for MnAPSO-5 (Example 31) was:

| Component | Weight Percent |
|---|---|
| Al$_2$O$_3$ | 31.8 |
| P$_2$O$_5$ | 46.4 |
| MnO | 4.1 |
| SiO$_2$ | 3.0 |
| Carbon | 5.2 |
| LOI* | 14.5 |

*LOI = Loss on Ignition

The above chemical analysis gives an overall product composition in molar oxide ratios (anhydrous basis) of: 0.058 MnO; 0.312Al$_2$O$_3$:0.327P$_2$O$_5$:0.050SiO$_2$; and a formula (anhydrous basis) of:
0.05R(Mn$_{0.04}$Al$_{0.45}$P$_{0.47}$Si$_{0.04}$)O$_2$ (b) The chemical analysis of MnAPSO-11 (Example 24) was:

| Component | Weight Percent |
|---|---|
| Al$_2$O$_3$ | 32.5 |
| P$_2$O$_5$ | 46.7 |
| MnO | 4.3 |
| SiO$_2$ | 2.1 |
| Carbon | 4.1 |
| LOI* | 14.0 |

*LOI = Loss on Ignition

The above chemical analysis gives an overall product composition in molar oxide ratios (anhydrous basis) of: 0.061MnO; 0.319Al$_2$O$_3$; 0.329P$_2$O$_5$; 0.035SiO$_2$; and a formula (anhydrous basis) of:
0.06R(Mn$_{0.04}$Al$_{0.46}$P$_{0.47}$Si$_{0.03}$)O$_2$ (c) The chemical analysis for MnAPSO-20 (Example 46) was:

| Component | Weight Percent |
|---|---|
| Al$_2$O$_3$ | 27.3 |
| P$_2$O$_5$ | 39.6 |
| MnO | 4.6 |
| SiO$_2$ | 8.0 |
| Carbon | 8.4 |
| LOI* | 19.4 |

*LOI = Loss on Ignition

The above chemical analysis gives an overall product composition in molar oxide ratios (anhydrous basis) of: 0.065 MnO; 0.268Al$_2$O$_3$:0.279P$_2$O$_5$:0.133SiO$_2$; and a formula (anhydrous basis) of:
0.18R(Mn$_{0.05}$Al$_{0.41}$P$_{0.43}$Si$_{0.10}$)O$_2$ (d) The chemical analysis of MnAPSO-31 was:

| Component | Weight Percent |
|---|---|
| Al$_2$O$_3$ | 31.8 |
| P$_2$O$_5$ | 43.8 |
| MnO | 3.2 |
| SiO$_2$ | 2.6 |
| Carbon | 2.9 |
| LOI* | 16.7 |

*LOI = Loss on Ignition

The above chemical analysis gives an overall product composition in molar oxide ratios (anhydrous basis) of: 0.058MnO; 0.312Al$_2$O$_3$; 0.309P$_2$O$_5$; 0.043SiO$_2$; and a formula (anhydrous basis) of:
0.04R(Mn$_{0.04}$Al$_{0.47}$P$_{0.46}$Si$_{0.03}$)O$_2$ (e) The chemical analysis of MnAPSO-34 (Example 6) was:

| Component | Weight Percent |
|---|---|
| Al$_2$O$_3$ | 25.0 |
| P$_2$O$_5$ | 35.8 |
| MnO | 7.9 |
| SiO$_2$ | 11.6 |
| Carbon | 3.3 |
| LOI* | 19.7 |

*LOI = Loss on Ignition

The above chemical analysis gives an overall product composition in molar oxide ratios (anhydrous basis) of: 0.11MnO; 0.25Al$_3$O$_3$; 0.19P$_2$O$_5$; 0.19SiO$_2$; and a formula (anhydrous basis) of:
0.04R(Mn$_{0.09}$Al$_{0.38}$P$_{0.39}$Si$_{0.15}$)O$_2$ (f) The chemical analysis of MnAPSO-35 (Example 23) was:

| Component | Weight Percent |
|---|---|
| Al$_2$O$_3$ | 25.2 |
| P$_2$O$_5$ | 41.3 |
| MnO | 7.1 |
| SiO$_2$ | 4.2 |
| Carbon | 12.8 |
| LOI* | 21.3 |

*LOI = Loss on Ignition

The above chemical analysis gives an overall product composition in molar oxide ratios (anhydrous basis) of: 0.100MnO; 0.247Al$_2$O$_3$; 0.291P$_2$O$_5$; 0.07SiO$_2$; and a formula (anhydrous basis) of:
0.13R(Mn$_{0.08}$Al$_{0.40}$P$_{0.47}$Si$_{0.06}$)O$_2$ (g) The chemical analysis of MnAPSO-36 (Example 59) was:

| Component | Weight Percent |
|---|---|
| $Al_2O_3$ | 27.7 |
| $P_2O_5$ | 37.2 |
| MnO | 4.6 |
| $SiO_2$ | 9.5 |
| Carbon | 3.0 |
| LOI* | 19.6 |

*LOI = Loss on Ignition

The above chemical analysis gives an overall product composition in molar oxide ratios anhydrous basis) of: 0.065MnO; 0.272$Al_2O_3$; 0.262$P_2O_5$; 0.158$SiO_2$; and a formula (anhydrous basis) of:

0.03R($Mn_{0.05}Al_{0.42}P_{0.41}Si_{0.12}$)$O_2$ (h) The chemical analysis of MnAPSO-44 (Example 64) was:

| Component | Weight Percent |
|---|---|
| $Al_2O_3$ | 25.8 |
| $P_2O_5$ | 36.6 |
| MnO | 4.4 |
| $SiO_2$ | 9.7 |
| Carbon | 2.5 |
| LOI* | 23.1 |

*LOI = Loss on Ignition

The above chemical analysis gives an overall product composition in molar oxide ratios (anhydrous basis) of: 0.062MnO; 0.253$Al_2O_3$; 0.258$P_2O_5$; 0.161$SiO_2$; and a formula (anhydrous basis) of:

0.04R($Mn_{0.05}Al_{0.41}P_{0.41}Si_{0.13}$)$O_2$ (i) The chemical analysis of MnAPSO-47 (Example 49) was:

| Component | Weight Percent |
|---|---|
| $Al_2O_3$ | 27.6 |
| $P_2O_5$ | 36.2 |
| MnO | 5.0 |
| $SiO_2$ | 5.7 |
| Carbon | 9.9 |
| LOI* | 25.1 |

*LOI = Loss on Ignition

The above chemical analysis gives an overall product composition in molar oxide ratios (anhydrous basis) of: 0.071MnO; 0.271$Al_2O_3$; 0.255$P_2O_5$; 0.095$SiO_2$; and a formula (anhydrous basis) of:

0.17R($Mn_{0.06}Al_{0.44}P_{0.42}Si_{0.08}$)$O_2$

EXAMPLE 67

EDAX (energy dispersive analysis by x-ray) microprobe analysis in conjunction with SEM (scanning electron microscope) was carried out on clear crystals from the products of certain examples, as identified in parenthesis hereinafter. Analysis of crystals having a morphology characteristic of each MnAPSO product gave the following analysis based on relative peak heights:

| Average of Spot Probes | |
|---|---|
| (a) MnAPSO-5 (Example 4): | |
| Mn | 0.5 |
| Al | 8.0 |
| P | 9.5 |
| Si | 0.7 |
| (b) MnAPSO-11 (Example 24: | |
| Mn | 1.0 |
| Al | 8.0 |

-continued

| Average of Spot Probes | |
|---|---|
| P | 9.5 |
| Si | 1.5 |
| (c) MnAPSO-20 (Example 46): | |
| Mn | 0.8 |
| Al | 8.2 |
| P | 9.4 |
| Si | 1.7 |
| (d) MnAPSO-34 (Example 6): | |
| Mn | 1.3 |
| Al | 7.0 |
| P | 9.0 |
| Si | 1.5 |
| (e) MnAPO-35 (Example 23): | |
| Mn | 1.0 |
| Al | 7.0 |
| P | 10.0 |
| Si | 1.2 |
| (f) MnAPSO-36 (Example 59): | |
| Mn | 0.8 |
| Al | 9.3 |
| P | 9.9 |
| Si | 1.6 |
| (g) MnAPSO-44 (Example 42): | |
| Mn | 0.7 |
| Al | 9.0 |
| P | 10.0 |
| Si | 1.7 |
| (h) MnAPSO-44 (Example 64): | |
| Mn | 1.1 |
| Al | 8.7 |
| P | 10.0 |
| Si | 5.6 |
| (i) MnAPSO-47 (Example 49): | |
| Mn | 1.0 |
| Al | 9.0 |
| P | 9.5 |
| Si | 1.9 |

EXAMPLE 68

(a) The MnAPSO-5, prepared in Example 31, was subjected to x-ray analysis. The MnAPSO-5 was impure but the major phase was determined to have an x-ray powder diffraction pattern characterized by the following data:

| 2θ | d, (Å) | $I/I_o \times 100$ |
|---|---|---|
| 6.9* | 12.81 | 13 |
| 7.5 | 11.79 | 100 |
| 8.0* | 11.05 | 5 |
| 9.1* | 9.72 | 4 |
| 9.3* | 9.51 | 4 |
| 13.0 | 6.81 | 14 |
| 13.7* | 6.46 | 3 |
| 15.0 | 5.91 | 27 |
| 16.5* | 5.37 | 3 |
| 18.5* | 4.80 | 7 |
| 19.8 | 4.48 | 43 |
| 21.0 | 4.23 | 58 |
| 22.3 | 3.99 | 75 |
| 24.7 | 3.60 | 6 |
| 25.9 | 3.440 | 42 |
| 29.0 | 3.079 | 18 |
| 30.0 | 2.979 | 34 |
| 33.6 | 2.667 | 8 |
| 34.5 | 2.600 | 21 |
| 36.9 | 2.436 | 4 |
| 37.7 | 2.386 | 10 |
| 41.5 | 2.176 | 5 |
| 42.1 | 2.146 | 5 |
| 42.2 | 2.141 | 5 |
| 42.6 | 2.122 | 5 |
| 43.5 | 2.080 | 3 |
| 44.9 | 2.019 | 3 |
| 47.5 | 1.914 | 7 |

| 2θ | d, (Å) | I/Io × 100 |
|---|---|---|
| 51.4 | 1.778 | 5 |
| 51.9 | 1.762 | 3 |
| 55.5 | 1.656 | 5 |

*Peak may contain an impurity (b) A portion of the as-synthesized MnAPSO-5 of part (a) was calcined in air at 500° C. for about two (2) hours. The calcined product was characterized by the following x-ray powder diffraction pattern:

| 2θ | d, (Å) | I/Io × 100 |
|---|---|---|
| 7.4 | 11.95 | 100 |
| *7.8 | 11.33 | 4 |
| 12.9 | 6.86 | 25 |
| 15.0 | 5.91 | 21 |
| *16.5 | 5.37 | 3 |
| *16.7 | 5.31 | 3 |
| *17.5 | 5.07 | 5 |
| 19.8 | 4.48 | 40 |
| 21.2 | 4.19 | 40 |
| 22.5 | 3.95 | 43 |
| 26.0 | 3.427 | 30 |
| 29.1 | 3.069 | 11 |
| 30.1 | 2.969 | 35 |
| 33.7 | 2.660 | 5 |
| 34.6 | 2.592 | 19 |
| 37.1 | 2.423 | 4 |
| 37.9 | 2.374 | 6 |
| 42.5 | 2.127 | 4 |
| 43.1 | 2.099 | 3 |
| 46.0 | 1.973 | 3 |
| 47.9 | 1.899 | 5 |
| 55.8 | 1.647 | 4 |

*Peak may contain an impurity (c) The species denominated herein as MnAPSO-5 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_2Al_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-5 having a characteristic x-ray powder diffraction pattern which contains at least the d-spacings set forth in Table V as follows:

TABLE V

| 2θ | d, (Å) | Relative Intensity |
|---|---|---|
| 7.3–7.7 | 12.11–11.48 | vs |
| 14.7–15.1 | 6.03–5.87 | m |
| 19.6–19.9 | 4.53–4.46 | m |
| 20.8–21.3 | 4.27–4.17 | m |
| 22.1–22.6 | 4.02–3.93 | m |
| 29.8–30.2 | 2.998–2.959 | m |

(d) All of the MnAPSO-5 compositions, both as-synthesized and calcined, for which x-ray power diffraction data have presently been obtained have patterns which are within the generalized pattern of Table VI below:

TABLE VI

| 2θ | d, (Å) | I/Io × 100 |
|---|---|---|
| 7.3–7.7 | 12.11–11.48 | 100 |
| 12.7–13.0 | 6.97–6.81 | 14–27 |
| 14.7–15.1 | 6.03–5.87 | 20–60 |
| 19.6–19.9 | 4.53–4.46 | 36–51 |
| 20.8–21.3 | 4.27–4.17 | 29–58 |
| 22.1–22.6 | 4.02–3.93 | 30–75 |
| 24.5–24.7 | 3.63–3.60 | 4–6 |
| 25.7–26.1 | 3.466–3.414 | 25–42 |
| 28.8–29.2 | 3.100–3.058 | 10–30 |
| 29.8–30.2 | 2.998–2.959 | 34–50 |
| 33.4–33.8 | 2.683–2.652 | 4–10 |
| 34.3–34.7 | 2.614–2.585 | 19–44 |
| 36.7–37.2 | 2.449–2.417 | 3–4 |
| 37.5–38.0 | 2.398–2.368 | 5–20 |
| 41.3–41.5 | 2.186–2.176 | 3–5 |
| 41.9–42.1 | 2.156–2.146 | 4–5 |
| 42.0–42.2 | 2.151–2.141 | 3–5 |
| 42.4–42.6 | 2.132–2.122 | 3–5 |
| 43.1–43.5 | 2.099–2.080 | 3–5 |
| 44.7–44.9 | 2.027–2.019 | 3–5 |
| 46.0–46.1 | 1.973–1.969 | 3–4 |
| 47.3–47.6 | 1.922–1.910 | 5–7 |
| 47.9–48.0 | 1.899–1.895 | 4–5 |
| 51.2–51.4 | 1.784–1.778 | 5–7 |
| 51.7–51.9 | 1.768–1.762 | 3–5 |
| 55.3–55.9 | 1.661–1.645 | 2–7 |

EXAMPLE 69

(a) MnAPSO-11, as prepared in example 24, was subjected to x-ray analysis. The MnAPSO-11 was determined to have an x-ray powder diffraction pattern characterized by the following data:

| 2θ | d, (Å) | I/Io × 100 |
|---|---|---|
| 8.1 | 10.92 | 36 |
| 9.5 | 9.31 | 61 |
| 13.1 | 6.76 | 19 |
| 15.7 | 5.64 | 36 |
| 16.2 | 5.47 | 10 |
| 19.1 | 4.65 | 13 |
| 20.5 | 4.33 | 45 |
| 21.1 | 4.21 | 100 |
| 22.2 | 4.00 | 55 |
| 22.5 | 3.95 | 52 |
| 22.7 | 3.92 | 61 |
| 23.2 | 3.83 | 71 |
| 24.5 | 3.63 | 13 |
| 24.8 | 3.59 | 16 |
| 25.0 | 3.562 | 13 |
| 26.4 | 3.38 | 26 |
| 28.3 | 3.153 | 13 |
| 28.6 | 3.121 | 23 |
| 29.5 | 3.028 | 13 |
| 31.5 | 2.84 | 16 |
| 32.8 | 2.730 | 23 |
| 34.2 | 2.622 | 16 |
| 35.4 | 2.54 | 10 |
| 35.8 | 2.508 | 10 |
| 36.3 | 2.475 | 10 |
| 37.5 | 2.398 | 13 |
| 37.8 | 2.370 | 16 |
| 39.4 | 2.287 | 10 |
| 42.9 | 2.108 | 10 |
| 44.8 | 2.023 | 10 |
| 48.8 | 1.866 | 3 |
| 50.6 | 1.804 | 10 |
| 54.6 | 1.681 | 10 |

(b) A portion of the as-synthesized MnAPSO-11 of part (a) was calcined in air at 600° C. for about two (2)

hours. The calcined product was characterized by the following x-ray powder diffraction pattern:

| 2θ | d, (Å) | I/Io × 100 |
|---|---|---|
| 8.1 | 10.92 | 33 |
| 9.8 | 9.03 | 60 |
| 11.8 | 7.50 | 13 |
| 12.8 | 6.92 | 27 |
| 13.5 | 6.56 | 13 |
| 14.8 | 5.99 | sh |
| 16.1 | 5.51 | 67 |
| 19.5 | 4.55 | 27 |
| 19.9 | 4.46 | 40 |
| 20.4 | 4.35 | 33 |
| 21.5 | 4.13 | 73 |
| 21.8 | 4.08 | 100 |
| 22.2 | 4.00 | 73 |
| 22.4 | 3.97 | 80 |
| 23.5 | 3.79 | 73 |
| 24.3 | 3.66 | 27 |
| 25.8 | 3.453 | 33 |
| 26.7 | 3.339 | 27 |
| 27.3 | 3.267 | 33 |
| 27.8 | 3.209 | 33 |
| 28.5 | 3.132 | 27 |
| 29.5 | 3.028 | 33 |
| 29.8 | 2.998 | 40 |
| 30.4 | 2.940 | 27 |
| 31.8 | 2.814 | 20 |
| 32.6 | 2.747 | 33 |
| 34.0 | 2.637 | 20 |
| 35.5 | 2.529 | 27 |
| 37.1 | 2.423 | 20 |
| 37.4 | 2.404 | 20 |
| 38.2 | 2.356 | 20 |
| 38.6 | 2.332 | 27 |
| 41.0 | 2.201 | 20 |

(c) The species denominated herein as MnAPSO-11 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

$$mR:(Mn_2Al_xP_ySi_z)O_2$$

wherein "R" represents at least one organic templating agent present in the intracrystalline pore system; "m" represents the molar amount of "R" present per mole of $(Mn_2Al_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-11 having a characteristic x-ray powder diffraction pattern which contains at least the d-spacings set forth in Table VII as follows:

TABLE VII

| 2θ | d, (Å) | Relative Intensity |
|---|---|---|
| 9.4–9.8 | 9.41–9.03 | m |
| 16.1–16.2 | 5.50–5.47 | vw–m |
| 21.0–21.5 | 4.23–4.13 | m–vs |
| 22.1–22.2 | 4.02–4.00 | m |
| 22.4–22.5 | 3.97–3.95 | m–s |
| 23.1–23.5 | 3.85–3.79 | m |

(d) All of the MnAPSO-11 compositions, both as-synthesized and calcined, for which x-ray power diffraction data have presently been obtain have patterns which are within the generalized pattern of Table VIII below:

TABLE VIII

| 2θ | d, (Å) | I/Io × 100 |
|---|---|---|
| 8.0–8.1 | 11.05–10.92 | 31–36 |
| 9.4–9.8 | 9.41–9.03 | 56–61 |
| 11.8 | 7.50 | 13 |
| 12.8–13.1 | 6.92–6.76 | 17–27 |
| 13.5 | 6.56 | 13 |
| 14.8 | 5.99 | sh |
| 15.6–15.7 | 5.68–5.64 | 33–36 |
| 16.1–16.2 | 5.50–5.47 | 8–67 |
| 19.0–19.5 | 4.68–4.55 | 8–27 |
| 19.9 | 4.46 | 40 |
| 20.4–20.5 | 4.35–4.33 | 33–45 |
| 21.0–21.5 | 4.23–4.13 | 73–100 |
| 21.8 | 4.08 | 100 |
| 22.1–22.2 | 4.02–4.00 | 55–73 |
| 22.4–22.5 | 3.97–3.95 | 52–80 |
| 22.6–22.7 | 3.93–3.92 | 61 |
| 23.1–23.5 | 3.85–3.79 | 69–73 |
| 24.3–24.5 | 3.66–3.63 | 11–27 |
| 24.7–24.8 | 3.60–3.59 | 14–16 |
| 24.9–25.0 | 3.58–3.562 | sh–13 |
| 25.8 | 3.453 | 33 |
| 26.3–26.7 | 3.389–3.339 | 25–27 |
| 27.3 | 3.267 | 33 |
| 27.8 | 3.209 | 33 |
| 28.2–28.3 | 3.164–3.153 | 11–13 |
| 28.5–28.6 | 3.132–3.121 | 22–27 |
| 29.4–29.5 | 3.038–3.028 | 11–33 |
| 29.8 | 2.998 | 40 |
| 30.4 | 2.940 | 27 |
| 31.4–31.8 | 2.849–2.814 | 14–20 |
| 32.6–32.8 | 2.747–2.730 | 19–33 |
| 34.0–34.2 | 2.637–2.622 | 14–20 |
| 35.3–35.5 | 2.543–2.529 | sh–27 |
| 35.7–35.8 | 2.515–2.508 | 8–10 |
| 36.2–26.3 | 2.481–2.475 | 8–10 |
| 37.1 | 2.423 | 20 |
| 37.4–37.5 | 2.404–2.398 | 11–20 |
| 37.7–37.8 | 2.386–2.380 | 16–17 |
| 38.2 | 2.356 | 20 |
| 38.6 | 2.332 | 27 |
| 39.3–39.4 | 2.292–2.287 | 8–10 |
| 41.0 | 2.201 | 20 |
| 42.8–42.9 | 2.113–2.108 | 8–10 |
| 44.7–44.8 | 2.027–2.023 | 8–10 |
| 48.7–48.8 | 1.870–1.866 | 3–5 |
| 50.5–50.6 | 1.807–1.804 | 8–10 |
| 54.5–54.6 | 1.684–1.681 | 8–10 |

EXAMPLE 70

(a) MnAPSO-16, as prepared in example 14 was subjected to x-ray analysis. The MnAPSO-16 was determined to have an x-ray powder diffraction pattern characterized by the following data:

| 2θ | d, (Å) | I/Io × 100 |
|---|---|---|
| 8.6* | 10.28 | 8 |
| 11.0* | 8.04 | 23 |
| 11.4 | 7.76 | 48 |
| 13.3* | 6.66 | 11 |
| 15.9* | 5.57 | 5 |
| 17.3* | 5.13 | 24 |
| 17.7* | 5.01 | 8 |
| 18.7 | 4.75 | 40 |
| 21.1* | 4.21 | 19 |
| 21.9** | 4.06 | 100 |
| 23.0 | 3.87 | 13 |
| 23.2* | 3.83 | 10 |
| 23.7* | 3.75 | 5 |
| 25.1 | 3.548 | 5 |
| 26.6** | 3.351 | 26 |
| 26.7* | 3.339 | (sh) |
| 27.8 | 3.209 | 5 |
| 28.8* | 3.100 | 15 |

-continued

| 2θ | d, (Å) | I/Io × 100 |
|---|---|---|
| 29.0 | 3.079 | 15 |
| 29.8 | 2.998 | 24 |
| 32.0* | 2.797 | 16 |
| 32.6 | 2.747 | 7 |
| 34.7** | 2.585 | 10 |
| 35.7* | 2.515 | 5 |
| 37.8 | 2.380 | 11 |
| 39.7 | 2.270 | 5 |
| 42.0* | 2.151 | 5 |
| 44.2 | 2.049 | 5 |
| 48.5** | 1.877 | 10 |
| 49.4* | 1.845 | 5 |
| 52.4 | 1.746 | 5 |
| 54.7 | 1.678 | 5 |

*Impurity Peak
**Peak may contain impurity (b) A portion of the as-synthesized MnAPSO-16 of part (a) was calcined in nitrogen at 600° C. for about 2 hours. The calcined product was characterized by the following x-ray powder diffraction pattern:

| 2θ | d, (Å) | I/Io × 100 |
|---|---|---|
| 11.5 | 7.69 | 100 |
| 13.3* | 6.66 | 9 |
| 18.6 | 4.77 | 25 |
| 20.3* | 4.37 | 44 |
| 20.5* | 4.33 | 41 |
| 21.5 | 4.13 | 66 |
| 21.9** | 4.06 | 72 |
| 22.9 | 3.88 | 31 |
| 23.5* | 3.79 | 13 |
| 26.5** | 3.363 | 31 |
| 27.9 | 3.198 | 13 |
| 29.0 | 3.079 | 19 |
| 29.7 | 3.008 | 34 |
| 32.6 | 2.747 | 13 |
| 34.7** | 2.585 | 13 |
| 35.6* | 2.522 | 16 |
| 37.8 | 2.380 | 13 |
| 48.2** | 1.888 | 9 |

*Impurity Peak
**Peak may contain impurity (c) The species denominated herein as MnAPSO-16 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compostional area defined by points A, B, C, D and E of FIG. 1, more preferably by the tetragonal compostional area defined by points a, b, c, and d of FIG. 2, said MnAPSO-16 having a characteristic x-ray powder diffraction pattern which contains at least the d-spacings set forth in Table IX as follows:

TABLE IX

| 2θ | d, (Å) | Relative Intensity |
|---|---|---|
| 11.4–11.5 | 7.76–7.69 | m–vs |

TABLE IX-continued

| 2θ | d, (Å) | Relative Intensity |
|---|---|---|
| 18.6–18.7 | 4.77–4.75 | m |
| 21.9 | 4.06 | m–vs |
| 22.9–23.0 | 3.88–3.87 | w–m |
| 26.5–26.6 | 3.363–3.351 | m |
| 29.7–29.8 | 3.008–2.998 | m |

(d) All of the MnAPSO-16 compositions, both as-synthesized and calcined, for which x-ray power diffraction data have presently been obtain have patterns which are within the generalized pattern of Table X below:

TABLE X

| 2θ | d, (Å) | I/Io × 100 |
|---|---|---|
| 11.4–11.5 | 7.76–7.69 | 48–100 |
| 18.6–18.7 | 4.77–4.75 | 25–40 |
| 21.9* | 4.06 | 72–80 |
| 22.9–23.0 | 3.88–3.87 | 13–31 |
| 26.5–26.6* | 3.363–3.351 | 26–31 |
| 27.8–27.9 | 3.209–2.198 | 5–13 |
| 29.0 | 3.079 | 15–19 |
| 29.7–29.8 | 3.008–2.998 | 24–34 |
| 32.6 | 2.747 | 7–14 |
| 34.7* | 2.585 | 9–14 |
| 37.8 | 2.380 | 11–15 |
| 39.7 | 2.270 | 5–6 |
| 44.2 | 2.049 | 5–6 |
| 48.2–48.5* | 1.888–1.877 | 9–12 |
| 49.4 | 1.845 | 4–5 |
| 52.4 | 1.746 | 4–5 |
| 54.7 | 1.678 | 4–5 |

*Peak might contain an impurity

EXAMPLE 71

(a) MnAPSO-20, as prepared in example 46 was subjected to x-ray analysis. The MnAPSO-20 was determined to have an x-ray powder diffraction pattern characterized by the following data:

| 2θ | d, (Å) | I/Io × 100 |
|---|---|---|
| 14.0 | 6.35 | 49 |
| 19.8 | 4.49 | 43 |
| 22.1 | 4.02 | 3 |
| 23.7* | 3.75 | 1 |
| 24.3 | 3.67 | 100 |
| 28.1 | 3.177 | 13 |
| 31.5 | 2.842 | 11 |
| 34.6 | 2.595 | 16 |
| 37.5 | 2.400 | 2 |
| 40.1 | 2.247 | 4 |
| 42.7 | 2.118 | 4 |
| 47.4 | 1.917 | 4 |
| 51.8 | 1.764 | 7 |

*Peak may contain an impurity (b) A portion of the as-synthesized MnAPSO-20 of part (a) was calcined in air at 500° C. for about 1 hour. The calcined product was characterized by the following x-ray powder diffraction pattern:

| 2θ | d, (Å) | Relative Intensity |
|---|---|---|
| 7.1 | 12.51 | 2 |
| 14.0 | 6.33 | 100 |
| 19.8 | 4.48 | 40 |
| 22.2 | 4.00 | 4 |
| 24.3 | 3.66 | 99 |
| 28.2 | 3.168 | 17 |
| 31.6 | 2.835 | 15 |
| 34.7 | 2.589 | 17 |
| 40.2 | 2.243 | 3 |

-continued

| 2θ | d, (Å) | Relative Intensity |
|---|---|---|
| 42.7 | 2.116 | 4 |
| 47.5 | 1.913 | 4 |

(c) The species denominated herein as MnAPSO-20 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compostional area defined by points A, B, C, D and E of FIG. 1, more preferably by the tetragonal compostional area defined by points a, b, c and d of FIG. 2, said MnAPSO-20 having a characteristic x-ray powder diffraction pattern which contains at least the d-spacings set forth in Table XI as follows:

TABLE XI

| 2θ | d, (Å) | Relative Intensity |
|---|---|---|
| 13.904–13.998 | 6.3692–6.3263 | m–vs |
| 19.723–19.818 | 4.5011–4.4918 | m |
| 24.223–24.329 | 3.6742–3.6584 | vs |
| 28.039–28.163 | 3.1822–3.1684 | w |
| 31.434–31.560 | 2.8458–2.8348 | w |
| 34.527–34.652 | 2.5976–2.5866 | w |

(d) All of the MnAPSO-20 compositions, both as-synthesized and calcined for which x-ray power diffraction data have presently been obtain have patterns which are within the generalized pattern of Table XII below:

TABLE XII

| 2θ | d, (Å) | I/Io × 100 |
|---|---|---|
| 13.904–13.998 | 6.3692–6.3263 | 49–100 |
| 19.723–19.818 | 4.5011–4.4918 | 40–43 |
| 22.091–22.200 | 4.0236–4.0041 | 3–4 |
| 24.223–24.329 | 3.6742–3.6584 | 99–100 |
| 28.039–28.163 | 3.1822–3.1684 | 13–17 |
| 31.434–31.560 | 2.8458–2.8348 | 11–15 |
| 34.527–34.652 | 2.5976–2.5886 | 15–17 |
| 34.413–27.465 | 2.2501–2.4004 | 2 |
| 40.071–40.207 | 2.2501–2.2428 | 3–4 |
| 42.627–42.730 | 2.1209–2.1160 | 3–4 |
| 47.383–47.519 | 1.9185–1.9134 | 3–4 |
| 51.790–51.840 | 1.7652–1.7636 | 7 |

EXAMPLE 72

(a) MnAPSO-31, as prepared in example 54 was subjected to x-ray analysis. MnAPSO-31 was determined to have an x-ray powder diffraction pattern characterized by the following data:

| 2θ | d, (Å) | I/Io × 100 |
|---|---|---|
| 7.9 | 11.22 | 4 |
| 8.6 | 10.27 | 61 |
| 17.2 | 5.17 | 5 |

-continued

| 2θ | d, (Å) | I/Io × 100 |
|---|---|---|
| 18.5 | 4.81 | 4 |
| 20.4 | 4.36 | 49 |
| 21.2 | 4.19 | 4 |
| 22.0 | 4.04 | 30 |
| 22.1 | 4.02 | 32 |
| 22.7 | 3.92 | 100 |
| 25.3 | 3.526 | 5 |
| 25.8 | 3.459 | 3 |
| 28.1 | 3.181 | 12 |
| 29.8 | 2.995 | 6 |
| 31.8 | 2.812 | 22 |
| 35.2 | 2.548 | 9 |
| 36.2 | 2.482 | 3 |
| 37.3 | 2.411 | 3 |
| 37.8 | 2.382 | 3 |
| 38.3 | 2.353 | 3 |
| 38.4 | 2.346 | 3 |
| 39.4 | 2.285 | 3 |
| 39.8 | 2.266 | 3 |
| 40.3 | 2.241 | 3 |
| 46.8 | 1.942 | 3 |
| 48.8 | 1.866 | 2 |
| 51.8 | 1.766 | 5 |
| 55.6 | 1.654 | 2 |

(b) A portion of the as-synthesized MnAPSO-31 of part (a) was calcined in air at 500° C. for about 1.5 hours. The calcined product was characterized by the following x-ray powder diffraction pattern:

| 2θ | d, (Å) | I/Io × 100 |
|---|---|---|
| 8.6 | 10.31 | 58 |
| 14.8 | 5.98 | 4 |
| 17.1 | 5.18 | 9 |
| 18.5 | 4.81 | 4 |
| 20.4 | 4.36 | 52 |
| 22.1 | 4.03 | 44 |
| 22.7 | 3.92 | 100 |
| 25.3 | 3.526 | 7 |
| 25.8 | 3.460 | 8 |
| 28.1 | 3.181 | 15 |
| 29.8 | 2.998 | 11 |
| 31.1 | 2.879 | 3 |
| 31.8 | 2.811 | 33 |
| 35.3 | 2.546 | 11 |
| 36.3 | 2.477 | 6 |
| 37.3 | 2.409 | 3 |
| 37.8 | 2.383 | 3 |
| 38.3 | 2.348 | 3 |
| 39.4 | 2.289 | 4 |
| 40.3 | 2.236 | 3 |
| 45.4 | 2.000 | 3 |
| 46.8 | 1.942 | 5 |
| 47.6 | 1.909 | 4 |
| 48.9 | 1.864 | 3 |
| 51.7 | 1.767 | 6 |

(c) The species denominated herein as MnAPSO-31 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-31 having a characteristic x-ray powder diffraction pattern which contains at least the d-spacings set forth in Table XIII as follows:

TABLE XIII

| 2θ | d, (Å) | Relative Intensity |
|---|---|---|
| 8.482–9.501 | 10.4240–9.3084 | m |
| 20.222–20.353 | 4.3913–4.3632 | m |
| 21.879–21.993 | 4.0622–4.0415 | m |
| 22.071–22.088 | 4.0272–4.0242 | m |
| 22.587–22.698 | 3.9364–3.9174 | vs |
| 31.724–31.836 | 2.8546–2.8108 | m |

(d) All of the MnAPSO-31 compositions, both as-synthesized and calcined for which x-ray power diffraction data have presently been obtain have patterns which are within the generalized pattern of Table XIV below:

TABLE XIV

| 2θ | d, (Å) | I/Io × 100 |
|---|---|---|
| 7.694–7.883 | 11.4904–11.2145 | 2–4 |
| 8.482–9.501 | 10.4240–9.3084 | 58–66 |
| 14.756–14.822 | 6.0034–5.9767 | 2–4 |
| 17.016–17.158 | 5.2105–5.1679 | 5–9 |
| 18.310–18.466 | 4.8451–4.8046 | 3–4 |
| 20.222–20.353 | 4.3913–4.3632 | 45–52 |
| 21.032–21.221 | 4.2238–4.1867 | 4–5 |
| 21.879–21.993 | 4.0622–4.0415 | 30–51 |
| 22.071–22.088 | 4.0272–4.0242 | 32–44 |
| 22.587–22.698 | 3.9364–3.9174 | 100 |
| 23.164–23.190 | 3.8398–3.8355 | 2–3 |
| 25.115–25.260 | 3.5457–3.5256 | 4–7 |
| 25.663–25.757 | 3.4712–3.4588 | 3–8 |
| 27.922–28.050 | 3.1953–3.1809 | 12–15 |
| 29.701–29.831 | 3.0078–2.9950 | 6–11 |
| 31.068–31.315 | 2.8785–2.8564 | 2–3 |
| 31.724–31.836 | 2.8564–2.8108 | 21–33 |
| 35.117–35.251 | 2.5553–2.5460 | 9–11 |
| 35.871 | 2.5033 | 1 |
| 36.070–36.261 | 2.4900–2.4730 | 2–6 |
| 37.123–37.325 | 2.4217–2.4091 | 2–3 |
| 37.628–27.763 | 2.3904–2.3822 | 2–3 |
| 38.163–38.254 | 2.3581–2.3527 | 2–3 |
| 38.334–38.367 | 2.3480–2.3461 | 3 |
| 39.285–39.442 | 2.2933–2.2845 | 3–4 |
| 39.654–39.772 | 2.2728–2.2663 | 2–4 |
| 40.111–40.337 | 2.2480–2.2359 | 2–3 |
| 45.179–45.354 | 2.0069–1.9996 | 2–3 |
| 46.617–46.786 | 1.9483–1.9416 | 3–5 |
| 47.454–47.631 | 1.9158–1.9091 | 2–4 |
| 48.610–48.846 | 1.8729–1.8644 | 2–3 |
| 50.679–50.750 | 1.8012–1.7989 | 2 |
| 51.588–51.766 | 1.7716–1.7659 | 4–6 |
| 55.410–55.557 | 1.6581–1.6541 | 2 |

EXAMPLE 73

(a) MnAPSO-34, as prepared in example 11 was subjected to x-ray analysis. MnAPSO-34 was determined to have an x-ray powder diffraction pattern characterized by the following data:

| 2θ | d, (Å) | I/Io × 100 |
|---|---|---|
| 9.6 | 9.21 | 100 |
| 12.9 | 6.86 | 17 |
| 14.2 | 6.24 | 15 |
| 16.1 | 5.51 | 33 |
| 18.1 | 4.90 | 23 |
| 20.6 | 4.31 | 69 |
| 22.3 | 3.99 | 10 |
| 23.1 | 3.85 | 8 |

-continued

| 2θ | d, (Å) | I/Io × 100 |
|---|---|---|
| 25.2 | 3.534 | 25 |
| 25.8 | 3.453 | 19 |
| 27.5 | 3.243 | 10 |
| 28.4 | 3.143 | 10 |
| 29.5 | 3.028 | 10 |
| 30.5 | 2.931 | 27 |
| 31.2 | 2.867 | 23 |
| 33.8 | 2.652 | 8 |
| 34.3 | 2.614 | 12 |
| 36.3 | 2.475 | 8 |
| 43.0 | 2.103 | 6 |
| 43.5 | 2.080 | 6 |
| 47.5 | 1.914 | 6 |
| 48.9 | 1.863 | 8 |
| 50.9 | 1.794 | 6 |
| 53.0 | 1.728 | 6 |
| 55.7 | 1.650 | 6 |

(b) A portion of the as-synthesized MnAPSO-34 of part (a) was calcined in nitrogen at 425° C. for about 2 hours. The calcined product was characterized by the following x-ray powder diffraction pattern:

| 2θ | d, (Å) | I/Io × 100 |
|---|---|---|
| 9.6 | 9.21 | 100 |
| 13.0 | 6.86 | 25 |
| 14.1 | 6.28 | 5 |
| 16.2 | 5.47 | 15 |
| 17.9 | 4.96 | 15 |
| 19.1 | 4.65 | 5 |
| 20.8 | 4.27 | 37 |
| 22.2 | 4.00 | 5 |
| 22.4 | 3.97 | 5 |
| 23.2 | 3.83 | 7 |
| 25.2 | 3.534 | 15 |
| 26.0 | 3.427 | 12 |
| 27.7 | 3.220 | 4 |
| 28.3 | 3.153 | 5 |
| 29.7 | 3.008 | 4 |
| 30.7 | 2.912 | 17 |
| 31.3 | 2.849 | 11 |
| 32.4 | 2.763 | 3 |
| 34.6 | 2.592 | 5 |
| 36.2 | 2.481 | 4 |
| 38.8 | 2.321 | 3 |
| 39.8 | 2.265 | 3 |
| 43.1 | 2.099 | 3 |
| 43.6 | 2.076 | 3 |
| 47.8 | 1.903 | 1 |
| 49.0 | 1.859 | 3 |
| 51.0 | 1.791 | 3 |
| 53.3 | 1.719 | 4 |
| 54.6 | 1.681 | 3 |

(c) The species denominated herein as MnAPSO-34 is a molecular sieve having a three dimensional microporous crystalline framework structure of $MnO_2^{-2}$, $AlO_2^{-}$, $PO_2^{+}$ and $SiO_2$ tetrahedral oxide units and have an empirical chemical composition on an anhydrous basis expressed by the formula:

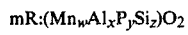

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-34 having a characteristic x-ray powder diffraction pattern which contains at least the d-spacings set forth in Table XV as follows:

TABLE XV

| 2θ | d, (Å) | Relative Intensity |
|---|---|---|
| 9.4–9.6 | 9.41–9.21 | vs |
| 15.9–16.2 | 5.57–5.47 | m |
| 20.4–20.8 | 4.35–4.27 | m-vs |
| 25.0–25.3 | 3.562–3.520 | w-m |
| 31.0–31.3 | 2.885–2.858 | w-m |
| 33.6–33.9 | 2.667–2.644 | m |

(d) All of the MnAPSO-34 compositions, both as-synthesized and calcined for which x-ray power diffraction data have presently been obtain have patterns which are within the generalized pattern of Table XIV below:

TABLE XIV

| 2θ | d, (Å) | I/Io × 100 |
|---|---|---|
| 9.4–9.6 | 9.41–9.21 | 100 |
| 12.7–13.0 | 6.97–6.86 | 17–25 |
| 14.0–14.2 | 6.33–6.24 | 5–17 |
| 15.9–16.2 | 5.57–5.47 | 15–44 |
| 17.9–18.1 | 4.96–4.90 | 15–32 |
| 19.1 | 4.65 | 5 |
| 20.4–20.8 | 4.35–4.27 | 37–92 |
| 22.1–22.3 | 4.02–3.99 | 5–16 |
| 22.4 | 3.97 | 5 |
| 22.9–23.2 | 3.88–3.83 | 7–16 |
| 25.0–25.3 | 3.562–3.520 | 15–36 |
| 25.8–26.0 | 3.453–3.427 | 12–19 |
| 27.3–27.7 | 3.267–3.220 | 4–28 |
| 28.2–28.5 | 3.164–3.132 | 5–16 |
| 29.3–29.7 | 3.048–3.008 | 4–16 |
| 30.3–30.7 | 2.950–2.912 | 10–17 |
| 31.0–31.3 | 2.885–2.849 | 11–40 |
| 32.4 | 2.763 | 3 |
| 33.6–33.9 | 2.667–2.644 | 23–32 |
| 34.3–34.6 | 2.614–2.592 | 5–12 |
| 36.2–36.4 | 2.481–2.468 | 4–16 |
| 38.8 | 2.321 | 3 |
| 39.8 | 2.265 | 3 |
| 43.0–43.1 | 2.103–2.099 | 3–12 |
| 43.5–43.6 | 2.080–2.076 | 3–12 |
| 47.4–47.8 | 1.918–1.903 | 1–12 |
| 48.8–49.0 | 1.866–1.859 | 3–12 |
| 50.8–51.0 | 1.797–1.791 | 3–12 |
| 52.9–53.3 | 1.731–1.719 | 4–12 |
| 54.6 | 1.681 | 3 |
| 55.6–55.8 | 1.653–1.647 | 6–12 |

EXAMPLE 74

(a) MnAPSO-35, as prepared in example 22 was subjected to x-ray analysis. MnAPSO-35 was determined to have an x-ray powder diffraction pattern characterized by the following data:

| 2θ | d, (Å) | I/Io × 100 |
|---|---|---|
| 8.6 | 10.28 | 14 |
| 10.9 | 8.12 | 45 |
| 13.4 | 6.61 | 23 |
| 15.9 | 5.57 | 11 |
| 17.4 | 5.10 | 80 |
| 17.8 | 4.98 | 16 |
| 20.9 | 4.25 | 57 |
| 21.9 | 4.06 | 100 |
| 23.2 | 3.83 | 34 |
| 24.8 | 3.59 | 9 |
| 25.7 | 3.466 | 7 |
| 26.9 | 3.314 | 21 |
| 28.3 | 3.153 | 50 |
| 29.1 | 3.069 | 11 |

-continued

| 2θ | d, (Å) | I/Io × 100 |
|---|---|---|
| 31.4 | 2.849 | 9 |
| 32.1 | 2.788 | 41 |
| 34.3 | 2.614 | 14 |
| 34.9 | 2.571 | 7 |
| 35.3 | 2.543 | 5 |
| 35.8 | 2.508 | 7 |
| 37.7 | 2.386 | 5 |
| 39.5 | 2.281 | 5 |
| 41.9 | 2.156 | 7 |
| 42.7 | 2.118 | 7 |
| 44.6 | 2.032 | 5 |
| 47.6 | 1.910 | 7 |
| 48.3 | 1.884 | 7 |
| 49.5 | 1.841 | 7 |
| 51.0 | 1.791 | 9 |
| 55.0 | 1.670 | 5 |
| 55.4 | 1.658 | 7 |

(b) A portion of the as-synthesized MnAPSO-35 of part (a) was calcined in nitrogen at 500° C. for about 2 hours. The calcined product was characterized by the following x-ray powder diffraction pattern:

| 2θ | d, (Å) | I/Io × 100 |
|---|---|---|
| 8.6 | 10.28 | 27 |
| 10.9 | 8.12 | 96 |
| 11.4 | 7.76 | 14 |
| 13.4 | 6.61 | 41 |
| 15.8 | 5.61 | 14 |
| 17.3 | 5.13 | 68 |
| 17.7 | 5.01 | sh |
| 20.8 | 4.27 | 64 |
| 21.9 | 4.06 | 100 |
| 23.3 | 3.82 | 32 |
| 24.8 | 3.59 | 23 |
| 25.7 | 3.466 | 18 |
| 26.9 | 3.314 | 27 |
| 28.3 | 3.153 | 59 |
| 29.1 | 3.069 | 23 |
| 31.4 | 2.849 | 18 |
| 32.2 | 2.780 | 46 |
| 34.2 | 2.622 | 18 |
| 34.8 | 2.578 | 14 |
| 35.8 | 2.508 | 9 |
| 41.9 | 2.156 | 9 |
| 42.5 | 2.127 | 9 |
| 44.6 | 2.032 | 9 |
| 47.4 | 1.918 | 9 |
| 48.2 | 1.888 | 9 |
| 49.4 | 1.845 | 9 |
| 51.0 | 1.791 | 14 |
| 55.2 | 1.664 | 9 |
| 55.7 | 1.650 | 9 |

(c) The species denominated herein as MnAPSO-35 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

$mR:(Mn_wAl_xP_ySi_z)O_2$ wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG.

1, more preferably by the tetragonal compostional area defined by points a, b, c and d of FIG. 2, said MnAPSO-35 having a characteristic x-ray powder diffraction pattern which contains at least the d-spacings set forth in Table XVII as follows:

TABLE XVII

| 2θ | d, (Å) | Relative Intensity |
| --- | --- | --- |
| 10.8–11.0 | 8.19–8.04 | m-vs |
| 13.4–13.7 | 6.61–6.46 | m-s |
| 17.2–17.5 | 5.16–5.07 | m-s |
| 20.8–21.0 | 4.27–4.23 | m |
| 21.8–22.3 | 4.08–3.99 | m-vs |
| 28.2–28.7 | 3.164–3.110 | m |

(d) All of the MnAPSO-35 compositions, both as-synthesized and calcined, for which x-ray power diffraction data have presently been obtain have patterns which are within the generalized pattern of Table XVIII below:

TABLE XVIII

| 2θ | d, (Å) | I/Io × 100 |
| --- | --- | --- |
| 8.5–8.7 | 10.40–10.16 | 13–31 |
| 10.8–11.0 | 8.19–8.04 | 44–100 |
| 11.4–11.5 | 7.76–7.69 | 8–14 |
| 13.3–13.4 | 6.66–6.61 | 22–41 |
| 13.4–13.7 | 6.61–6.46 | 31–81 |
| 15.8–15.9 | 5.61–5.57 | 10–14 |
| 17.2–17.5 | 5.16–5.07 | 38–82 |
| 17.7–18.0 | 5.01–4.93 | (sh)–18 |
| 20.8–21.0 | 4.27–4.23 | 44–46 |
| 21.8–22.3 | 4.08–3.99 | 56–100 |
| 23.1–23.6 | 3.85–3.77 | 31–34 |
| 24.7–25.2 | 3.60–3.534 | 13–31 |
| 25.6–25.8 | 3.480–3.453 | 4–25 |
| 26.8–27.4 | 3.326–3.255 | 19–44 |
| 28.2–28.7 | 3.164–3.110 | 50–59 |
| 29.0–29.6 | 3.079–3.018 | 10–31 |
| 31.3–31.4 | 2.858–2.849 | 9–18 |
| 32.0–32.8 | 2.797–2.730 | 31–46 |
| 34.2–34.3 | 2.622–2.614 | 11–18 |
| 34.8–34.9 | 2.578–2.571 | 4–14 |
| 35.2–35.3 | 2.550–2.543 | 5–7 |
| 35.7–35.8 | 2.515–2.508 | 4–9 |
| 37.6–37.7 | 2.392–2.386 | 4–5 |
| 39.4–39.5 | 2.287–2.281 | 4–7 |
| 41.8–42.0 | 2.161–2.151 | 6–9 |
| 42.5–42.8 | 2.127–2.113 | 5–9 |
| 44.5–44.7 | 2.036–2.027 | 5–9 |
| 47.4–47.7 | 1.918–1.907 | 6–9 |
| 48.2–48.4 | 1.888–1.881 | 6–9 |
| 49.4–49.6 | 1.845–1.838 | 6–9 |
| 50.9–51.1 | 1.794–1.787 | 5–14 |
| 54.9–55.2 | 1.672–1.664 | 5–9 |
| 55.3–55.7 | 1.661–1.650 | 6–9 |

EXAMPLE 75

(a) MnAPSO-36, as prepared in example 59 was subjected to x-ray analysis. The MnAPSO-36 was determined to have an x-ray powder diffraction pattern characterized by the following data:

| 2θ | d, (Å) | I/Io × 100 |
| --- | --- | --- |
| 7.4 | 11.88 | 15 |
| 7.9 | 11.22 | 100 |
| 8.2 | 10.82 | 33 |
| 13.5 | 6.55 | 5 |
| 15.8 | 5.61 | 10 |
| 16.4 | 5.41 | 31 |
| 19.1 | 4.66 | 14 |
| 20.7 | 4.28 | 34 |
| 21.2 | 4.19 | 4 |
| 21.7 | 4.10 | 16 |
| 22.0 | 4.04 | 14 |

-continued

| 2θ | d, (Å) | I/Io × 100 |
| --- | --- | --- |
| 22.5 | 3.96 | 15 |
| 23.0 | 3.87 | 5 |
| 23.9 | 3.73 | 6 |
| 27.2 | 3.276 | 15 |
| 27.9 | 3.193 | 3 |
| 28.3 | 3.153 | 8 |
| 29.0 | 3.079 | 7 |
| 30.2 | 2.958 | 4 |
| 30.3 | 2.951 | 4 |
| 32.0 | 2.798 | 8 |
| 34.8 | 2.579 | 7 |

(b) A portion of the as-synthesized MnAPSO-36 of part (a) was calcined in air at 500° C. for about 1 hour. The calcined product was characterized by the following x-ray powder diffraction pattern:

| 2θ | d, (Å) | I/Io × 100 |
| --- | --- | --- |
| 7.1 | 12.39 | 5 |
| 7.6 | 11.64 | 21 |
| 8.0 | 11.11 | 100 |
| 8.3 | 10.65 | 37 |
| 13.6 | 6.53 | 17 |
| 16.6 | 5.35 | 31 |
| 19.4 | 4.57 | 17 |
| 20.8 | 4.27 | 19 |
| 21.9 | 4.06 | 8 |
| 22.4 | 3.97 | 15 |
| 22.7 | 3.92 | 11 |
| 23.4 | 3.80 | 5 |
| 23.9 | 3.73 | 7 |
| 27.3 | 3.271 | 16 |
| 28.3 | 3.159 | 6 |
| 28.4 | 3.141 | 6 |
| 29.1 | 3.074 | 7 |
| 29.4 | 3.043 | 5 |
| 32.0 | 2.798 | 6 |

(c) The species denominated herein as MnAPSO-36 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

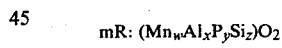

$$mR: (Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compostional area defined by points A, B, C, D and E of FIG. 1, more preferably by the tetragonal compositional area defined by points a, b, c and d of FIG. 2, said MnAPSO-36 having a characteristic x-ray powder diffraction pattern which contains at least the d-spacings set forth in Table XIX as follows:

TABLE XIX

| 2θ | d, (Å) | Relative Intensity |
| --- | --- | --- |
| 7.596 | 11.6382 | m |
| 7.628–7.981 | 11.5899–11.0771 | vs |
| 8.105–8.299 | 10.9084–10.6537 | m |
| 16.395–16.673 | 5.4066–5.3172 | m |
| 19.052–19.414 | 4.6580–4.5721 | w |

TABLE XIX-continued

| 2θ | d, (Å) | Relative Intensity |
|---|---|---|
| 20.744–20.871 | 4.2819–4.2560 | m |

(d) All of the MnAPSO-36 compositions, both as-synthesized and calcined for which x-ray power diffraction data have presently been obtain have patterns which are within the generalized pattern of Table XX below:

TABLE XX

| 2θ | d, (Å) | I/Io × 100 |
|---|---|---|
| 7.132 | 12.3939 | 5 |
| 7.596 | 11.6382 | 21 |
| 7.628–7.981 | 11.5899–11.0771 | 100 |
| 8.105–8.299 | 10.9084–10.6537 | 33–37 |
| 13.517–13.778 | 6.5503–6.4270 | 5–17 |
| 15.797–15.928 | 5.6099–5.5640 | 10–11 |
| 16.395–16.673 | 5.4066–5.3172 | 31–32 |
| 19.052–19.414 | 4.6580–4.5721 | 14–17 |
| 20.744–20.871 | 4.2819–4.2560 | 20–35 |
| 21.230 | 4.1848 | 4 |
| 21.655 | 4.1037 | 16 |
| 21.863–21.986 | 4.0651–4.0427 | 8–14 |
| 22.119–22.470 | 4.0186–3.9566 | 15 |
| 22.713–23.408 | 3.9150–3.8001 | 5–11 |
| 23.854–23.965 | 3.7301–3.7131 | 5–6 |
| 27.219–27.518 | 3.2761–3.2412 | 15–16 |
| 27.868–27.939 | 3.2014–3.1934 | 2–3 |
| 28.252 | 3.1587 | 6 |
| 28.304–28.536 | 3.1530–3.1279 | 6–8 |
| 29.003–29.268 | 3.0786–3.0513 | 6–7 |
| 29.347 | 3.0433 | 5 |
| 30.144–30.230 | 2.9646–2.9564 | 4 |
| 30.291–30.526 | 2.9505–2.9284 | 4 |
| 31.983–32.094 | 2.7982–2.7888 | 6–9 |
| 34.640–34.968 | 2.5894–2.5659 | 7 |

EXAMPLE 76

(a) MnAPSO-44, as prepared in example 64 was subjected to x-ray analysis. The MnAPSO-44 was determined to have an x-ray powder diffraction pattern characterized by the following data:

| 2θ | d, (Å) | I/Io × 100 |
|---|---|---|
| 9.4 | 9.39 | 100 |
| 13.0 | 6.83 | 20 |
| 13.7 | 6.45 | 4 |
| 16.1 | 5.52 | 43 |
| 17.3 | 5.12 | 5 |
| 19.0 | 4.68 | 7 |
| 20.7 | 4.29 | 84 |
| 21.7 | 4.09 | 21 |
| 22.6 | 3.94 | 8 |
| 23.1 | 3.86 | 9 |
| 24.4 | 3.65 | 58 |
| 26.1 | 3.409 | 22 |
| 27.8 | 3.205 | 10 |
| 29.7 | 3.012 | 5 |
| 30.1 | 2.969 | 16 |
| 30.8 | 2.900 | 50 |
| 32.5 | 2.753 | 4 |
| 32.9 | 2.721 | 6 |
| 34.8 | 2.577 | 3 |
| 35.5 | 2.528 | 9 |
| 38.5 | 2.336 | 2 |
| 39.2 | 2.299 | 2 |
| 40.0 | 2.255 | 2 |
| 42.2 | 2.143 | 3 |
| 42.5 | 2.125 | 3 |
| 43.6 | 2.076 | 2 |
| 47.3 | 1.922 | 2 |
| 48.2 | 1.890 | 7 |
| 48.7 | 1.870 | 4 |
| 50.3 | 1.814 | 7 |

-continued

| 2θ | d, (Å) | I/Io × 100 |
|---|---|---|
| 53.9 | 1.701 | 6 |

(b) A portion of the as-synthesized MnAPSO-44 of part (a) was calcined in air at 500° C. for about one (1) hour. The calcined product was characterized by the following x-ray powder diffraction pattern:

| 2θ | d, (Å) | I/Io × 100 |
|---|---|---|
| 9.6 | 9.21 | 100 |
| 13.1 | 6.79 | 26 |
| 14.2 | 6.26 | 3 |
| 16.2 | 5.46 | 12 |
| 18.0 | 4.93 | 18 |
| 19.3 | 4.60 | 3 |
| 20.9 | 4.25 | 28 |
| 22.3 | 3.99 | 3 |
| 23.4 | 3.80 | 3 |
| 25.3 | 3.526 | 13 |
| 26.3 | 3.387 | 9 |
| 28.5 | 3.137 | 3 |
| 28.6 | 3.123 | 4 |
| 29.9 | 2.990 | 2 |
| 30.0 | 2.976 | 2 |
| 30.6 | 2.921 | 3 |
| 31.1 | 2.875 | 7 |
| 31.8 | 2.811 | 2 |
| 32.1 | 2.791 | 2 |
| 35.1 | 2.560 | 3 |

(c) The species denominated herein as MnAPSO-44 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

$$mR: (Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compostional area defined by points a, b, c and d of FIG. 2, said MnAPSO-44 having a characteristic x-ray powder diffraction pattern which contains at least the d-spacings set forth in Table XXI as follows:

TABLE XXI

| 2θ | d, (Å) | Relative Intensity |
|---|---|---|
| 9.420–9.498 | 9.3883–9.3110 | vs |
| 16.062–16.131 | 5.5179–5.4944 | m |
| 20.715–20.790 | 4.2877–4.2725 | s |
| 24.396–24.424 | 3.6485–3.6444 | m |
| 26.143–26.184 | 3.4085–3.4032 | m |
| 30.833–30.853 | 2.8999–2.8981 | m |

(d) All of the MnAPSO-44 compositions, both as-synthesized and calcined, for which x-ray power diffraction data have presently been obtain have patterns which are within the generalized pattern of Table XXII below:

TABLE XXII

| 2θ | d, (Å) | I/Io × 100 |
|---|---|---|
| 9.420–9.498 | 9.3883–9.3110 | 100 |
| 12.930–12.958 | 6.8468–6.8318 | 20 |
| 13.738 | 6.4458 | 4 |
| 16.062–16.131 | 5.5179–5.4944 | 43 |
| 17.329–17.396 | 5.1173–5.0975 | 5 |
| 18.950–18.998 | 4.6828–4.6713 | 7 |
| 20.715–20.790 | 4.2877–4.2725 | 84 |
| 21.709–21.743 | 4.0937–4.0873 | 21 |
| 22.366–22.583 | 3.9748–3.9372 | 8 |
| 23.061–23.101 | 3.8566–3.8501 | 9 |
| 24.396–24.424 | 3.6485–3.6444 | 58 |
| 26.143–26.184 | 3.4085–3.4032 | 22 |
| 27.837–27.881 | 3.2049–3.1999 | 10 |
| 29.661 | 3.0117 | 5 |
| 30.002–30.096 | 2.9783–2.9692 | 16 |
| 30.833–20.853 | 2.8999–2.8981 | 50 |
| 32.520–32.562 | 2.7532–2.7498 | 4 |
| 32.900–32.918 | 2.7223–2.7208 | 6 |
| 34.812 | 2.5770 | 3 |
| 35.516–35.534 | 2.5275–2.5263 | 9 |
| 38.536 | 2.3361 | 2 |
| 38.185 | 2.2989 | 2 |
| 39.991 | 2.2545 | 2 |
| 42.162–42.177 | 2.1432–2.1425 | 3 |
| 42.533–42.541 | 2.1254–2.1250 | 3 |
| 43.607–73.621 | 2.0755–2.0749 | 2 |
| 47.283 | 1.9224 | 2 |
| 48.157–48.177 | 1.8895–1.8888 | 7 |
| 48.640–48.697 | 1.8719–1.8698 | 4 |
| 50.303–50.307 | 1.8138–1.8137 | 7 |
| 53.885–53.887 | 1.7014–1.7013 | 6 |

EXAMPLE 77

(a) MnAPSO-47, as prepared in example 49 was subjected to x-ray analysis. The MnAPSO-47 was determined to have an x-ray powder diffraction pattern characterized by the following data:

| 2θ | d, (Å) | I/Io × 100 |
|---|---|---|
| 4.8 | 18.44 | 1 |
| 9.4 | 9.38 | 100 |
| 12.9 | 6.89 | 5 |
| 13.9 | 6.40 | 3 |
| 16.0 | 5.56 | 9 |
| 17.5 | 5.06 | 4 |
| 18.9 | 4.69 | 3 |
| 20.5 | 4.32 | 30 |
| 21.8 | 4.08 | 4 |
| 22.4 | 3.98 | 1 |
| 22.9 | 3.88 | 3 |
| 24.6 | 3.61 | 11 |
| 25.9 | 3.445 | 7 |
| 27.6 | 3.234 | 2 |
| 27.9 | 3.199 | 1 |
| 29.5 | 3.033 | 2 |
| 30.5 | 2.930 | 10 |
| 30.8 | 2.901 | 7 |
| 31.5 | 2.845 | 1 |
| 33.2 | 2.700 | 1 |
| 34.4 | 2.604 | 2 |
| 34.8 | 2.576 | 1 |
| 35.7 | 2.516 | 2 |
| 38.4 | 2.343 | 1 |
| 39.2 | 2.297 | 1 |
| 39.6 | 2.277 | 1 |
| 42.4 | 2.132 | 1 |
| 43.3 | 2.091 | 1 |
| 47.6 | 1.911 | 1 |
| 48.6 | 1.874 | 5 |
| 50.3 | 1.813 | 2 |
| 53.2 | 1.722 | 1 |
| 54.0 | 1.698 | 1 |

(b) A portion of the as-synthesized MnAPSO-47 of part (a) was calcined in air at 500° C. for about one (1) hour. The calcined product was characterized by the following x-ray powder diffraction pattern:

| 2θ | d, (Å) | I/Io × 100 |
|---|---|---|
| 5.0 | 17.80 | 1 |
| 9.7 | 9.12 | 100 |
| 10.0 | 8.85 | 1 |
| 13.1 | 6.75 | 5 |
| 14.2 | 6.23 | 1 |
| 16.3 | 5.45 | 2 |
| 18.0 | 4.92 | 2 |
| 19.4 | 4.58 | 3 |
| 20.9 | 4.24 | 7 |
| 22.4 | 3.98 | 1 |
| 23.4 | 3.80 | 1 |
| 25.3 | 3.521 | 2 |
| 26.3 | 3.385 | 2 |
| 28.1 | 3.176 | 1 |
| 28.6 | 3.125 | 1 |
| 30.0 | 2.977 | 1 |
| 31.1 | 2.876 | 3 |
| 31.5 | 2.837 | 2 |
| 33.9 | 2.645 | 1 |
| 35.0 | 2.562 | 1 |
| 49.6 | 1.838 | 1 |

(c) The species denominated herein as MnAPSO-47 is a molecular sieve having a three dimensional microporous crystalline framework structure of $MnO_2^{-2}$, $AlO_2^-$, $PO_2^+$ and $SiO_2$ tetrahedral oxide units and have an empirical chemical composition on an anhydrous basis expressed by the formula:

$$mR: (Mn_wAl_xP_ySi_z)O_2$$

wherein "R" represents at least one organic templating agent present in the intracrystalline pore system; "m" represents the molar amount of "R" present per mole of $(Mn_2Al_xP_ySi_z)O_2$ and has a value of zero to about 0.3; and "w", "x", "y" and "z" represent the mole fractions of manganese, aluminum, phosphorus and silicon respectively, present as tetrahedral oxide, said mole fractions being within the pentagonal compositional area defined by points A, B, C, D and E of FIG. 1, more preferably by the tetragonal compositional area defined by points a, b, c and d of FIG. 2, said MnAPSO-47 having a characteristic x-ray powder diffraction pattern which contains at least the d-spacings set forth in Table XXIII as follows:

TABLE XXIII

| 2θ | d, (Å) | Relative Intensity |
|---|---|---|
| 9.434–9.696 | 9.3746–9.1214 | vs |
| 15.946–16.276 | 5.5579–5.4457 | vw |
| 20.539–20.940 | 4.3242–4.2423 | vw–m |
| 24.643 | 3.6125 | w |
| 30.511 | 2.9297 | w |
| 30.820–31.096 | 2.9011–2.8759 | vw |

(d) All of the MnAPSO-47 compositions, both as-synthesized and calcined for which x-ray power diffraction data have presently been obtain have patterns which are within the generalized pattern of Table XXIV below:

TABLE XXIV

| 2θ | d, (Å) | I/Io × 100 |
|---|---|---|
| 4.793–4.964 | 18.4368–17.8028 | 1 |
| 9.434–9.696 | 9.3746–9.1214 | 100 |
| 12.847–13.107 | 6.8907–6.7543 | 5 |
| 13.840–14.211 | 6.3983–6.2321 | 1–3 |
| 15.946–16.276 | 5.5579–5.4457 | 2–9 |
| 17.544–18.032 | 5.0550–4.9191 | 2–4 |
| 18.941–19.365 | 4.6851–4.5836 | 3 |

TABLE XXIV-continued

| 2θ | d. (Å) | I/Io × 100 |
|---|---|---|
| 20.539–20.940 | 4.3242–4.2423 | 6–30 |
| 21.811 | 4.0747 | 4 |
| 22.351–22.352 | 3.9775–3.9774 | 1 |
| 22.936 | 3.8773 | 3 |
| 23.401 | 3.8013 | 1 |
| 24.643 | 3.6125 | 11 |
| 25.294–25.864 | 3.5210 | 2–7 |
| 26.327–27.577 | 3.3851–3.2344 | 2 |
| 27.881–28.093 | 3.1992–3.1762 | 1 |
| 28.560 | 3.1253 | 1 |
| 29.448–30.019 | 3.0331–2.9767 | 1–2 |
| 30.511 | 2.9297 | 10 |
| 30.820–31.096 | 2.9011–2.8759 | 3–7 |
| 31.448–31.532 | 2.8446–2.8372 | 1–2 |
| 33.186–33.894 | 2.6995–2.6447 | 1 |
| 34.444 | 2.6037 | 2 |
| 34.834–35.026 | 2.5755–2.5618 | 1 |
| 35.685 | 2.5159 | 2 |
| 38.412 | 2.3434 | 1 |
| 39.223 | 2.2968 | 1 |
| 39.582 | 2.2768 | 1 |
| 42.403 | 2.1316 | 1 |
| 43.278 | 2.0905 | 1 |
| 47.595 | 1.9105 | 1 |
| 48.584–49.595 | 1.8739–1.8380 | 1–5 |
| 50.327 | 1.8130 | 2 |
| 53.205 | 1.7215 | 1 |
| 54.006 | 1.6979 | 1 |

EXAMPLE 78

The catalytic activity of MnAPSO compositions, calcined samples of the MnAPSO products of Examples 11, 21, 25, 31, 49, 55, 59 and 64 were tested for catalytic cracking.

The catalytic activity was determined using a reactor comprising a cylindrical quartz tube 254 mm. in length and 10.3 mm. I.D. In each test MnAPSO which were 20–40 mesh (U.S. std.) in size and in an amount of from 0.5 to 5 grams, the quantity being selected so that the conversion of n-butane was at least 5% and not more than 90% under the test conditions. Most of the MnAPSO samples had been previously calcined in air or nitrogen to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of onstream operation.

The pseudo-first-order rate constant ($k_A$) was calculated to determine the relative catalytic activity of the MnAPSO compositions. The $k_A$ value (cm³/g min) obtained for the MnAPSO compositions are set forth, below, in Table XXV:

TABLE XXV

| MnAPSO | Prepared in Example No.: | Rate Constant ($k_A$)* |
|---|---|---|
| MnAPSO-5 | 31 | 0.2 |
| MnAPSO-11 | 25 | 0.6 |
| MnAPSO-20 | 46 | 0.2 |
| MnAPSO-31 | 55 | 1.0; 0.5 |
| MnAPSO-34 | 11 | 3.1 |
| MnAPSO-35 | 21 | 0.1** |
| MnAPSO-36 | 59 | 0.3 |
| MnAPSO-44 | 64 | 1.5 |

TABLE XXV-continued

| MnAPSO | Prepared in Example No.: | Rate Constant ($k_A$)* |
|---|---|---|
| MnAPSO-47 | 49 | 1.7 |

*Prior to determination of the catalytic activity of a given MnAPSO, each was calcined as follows:
(a) Mn-APSO-5 was calcined at 500° C. in air for 2 hours;
(b) MnAPSO-11, MnAPSO-34 and MnAPSO-36 were calcined in situ;
(c) MnAPSO-31 was calcined in air at 500° C. for 1.5 hours and then at 600° C. for 1 hour;
(d) MnAPSO-35 was calcined at 500° C. in nitrogen for 1 hour; and
(e) MnAPSO-20, MnAPSO-44 and MnAPSO-47 were calcined at 500° C. in air for 1 hour.
**Less than 0.1

PROCESS APPLICATIONS

The MnAPSO compositions of the present invention are, in general, hydrophilic and adsorb water preferentially over common hydrocarbon molecules such as paraffins, olefins and aromatic species, e.g., benzene, xylenes and cumene. Thus, the MnAPSO as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These MnAPSOs are therefore suitably employed in the drying of reformer hydrogen streams and in the drying of oxygen, nitrogen or air prior to liquifaction.

The present MnAPSO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalyst compositions having silica or alumina bases. Of the general class, those species having pores larger than about 4 Å are preferred for catalytic applications.

Among the hydrocarbon conversion reactions catalyzed by MnAPSO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using MnAPSO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The MnAPSO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerizations processes in which feedstocks such as normal paraffins are converted to saturated branched chain isomers. Hydroisomerization is carried out at a temperature of from about 200° F. to 600° F., preferably 300° F. to 550°

F. with an LHSV value of from about 0.2 to 1.0. Hydrogen is supplied to the reactor in admixture with the hydrocarbon feedstock in molar proportions (hydrogen to hydrocarbon) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$–$C_{20}$. Contact time between the feedstock and the catalyst is generally relatively short to avoid undesireable side reactions such as olefin polymerization and paraffin cracking. LHSV values in the range of 0.1 to 10, preferably 1.0 to 6.0 are suitable.

The unique crystal structure of the present MnAPSO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with MnAPSO compositions using feedstocks such as gas oils, heavy naphthas, deasphalted crude oil residua, etc., with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the MnAPSO catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°-1000° F. are employed at moderate hydrogen pressures of about 300-1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residual and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°-900° F., while paraffins, naphthenes and alkyl aromatics are isomerized at temperatures of 700°-1000° F. Particularly desirable isomerization reactions contemplated herein include the conversion of n-heptene and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexene to isohexene, cyclohexene to methylcyclopentene etc. The preferred form of the catalyst is a combination of the MnAPSO with polyvalent metal compounds (such as sulfides) of metals of Group II-A, Group II-B and rare earth metals. For alkylation and dealkylation processes the MnAPSO compositions having pores of at least 5 Å are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In the alkylation of benzene, toluene and xylene, the preferred alkylating agents are olefins such as ethylene and propylene.

We claim:

1. Crystalline molecular sieves having three-dimensional microporous framework structures of $MnO_2$, $AlO_2$, $PO_2$ and $SiO_2$ tetrahedral oxide units having an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides, said mole fractions being such that they are within the pentagonal compositional area defined by points A, B, C, D and E of FIG. 1.

2. Crystalline molecular sieves according to claim 1 wherein said mole fractions "w", "x", "y" and "z" are within the tetragonal compositional area defined by points a, b, c and d of FIG. 2.

3. The crystalline molecular sieves of claims 1 or 2 having a characteristic x-ray powder diffraction pattern which contains at least the d-spacings set forth in Table A.

4. The crystalline molecular sieves of claims 1 or 2 having a characteristic x-ray powder diffraction pattern which contains at least the d-spacings set forth in Table B.

5. The crystalline molecular sieves or claims 1 or 2 having a characteristic x-ray powder diffraction pattern which contains at least the d-spacings set forth in Table C.

6. The crystalline molecular sieves of claims 1 or 2 having a characteristic x-ray powder diffraction pattern which contains at least the d-spacings set forth in Table D.

7. The crystalline molecular sieves of claims 1 or 2 having a characteristic x-ray powder diffraction pattern which contains at least the d-spacings set forth in Table E.

8. The crystalline molecular sieves of claims 1 or 2 having a characteristic x-ray powder diffraction pattern which contains at least the d-spacings set forth in Table F.

9. The crystalline molecular sieves of claims 1 or 2 having a characteristic x-ray powder diffraction pattern which contains at least the d-spacings set forth in Table G.

10. The crystalline molecular sieves of claims 1 or 2 having a characteristic x-ray powder diffraction pattern which contains at least the d-spacings set forth in Table H.

11. The crystalline molecular sieves of claims 1 or 2 having a characteristic x-ray powder diffraction pattern which contains at least the d-spacings set forth in Table J.

12. The crystalline molecular sieves of claims 1 or 2 having a characteristic x-ray powder diffraction pattern which contains at least the d-spacings set forth in Table K.

13. Process for preparing the crystalline molecular sieves of claim 1 having a three dimensional microporous framework structures which comprises providing a reaction mixture composition at an effective temperature and for an effective time sufficient to produce the molecular sieves of claim 1 being expressed in terms of molar oxide ratios as follows:

$$aR:(Mn_wAl_xP_ySi_z):bH_2O$$

wherein "R" is an organic templating agent; "a" is the amount of "R" and is an effective amount greater than zero to about 6; "b" has a value of from zero to about 500; and "w", "x", "y" and "z" represent the mole fractions, respectively, of manganese, aluminum, phosphorus and silicon in the $(Mn_wAl_xP_ySi_z)O_2$ constituent, and each has a value of at least 0.01.

14. Process according to claim 13 where "w", "x", "y" and "z" are within the area defined by points F, G, H, I and J of FIG. 3.

15. Process according to claim 13 wherein the source of phosphorus in the reaction mixture is orthophosphoric acid.

16. Process according to claim 13 wherein the source of phosphorus in the reacton mixture is orthophosphoric acid and the source of aluminum is at least one compound selected from the group consisting of pseudo-boehmite and aluminum alkoxide.

17. Process according to claim 16 wherein the aluminum alkoxide is aluminum isopropoxide.

18. Process according to claim 13 wherein the source of silicon is silica.

19. Process according to claim 13 wherein the source of manganese is selected from the group consisting of sulfates, carboxylates, chlorides, bromides, iodides and mixtures thereof.

20. Process according to claim 13 wherein the organic templating agent is a quaternary ammonium or quaternary phosphonium compound having the formula:

$$R_4X^+$$

wherein X is nitrogen or phosphorus and each R is an alkyl or aryl group containing from 1 to 8 carbon atoms.

21. Process according to claim 13 wherein the organic templating agent is an amine.

22. Process according to claim 13 or claim 14 wherein the templating agent is selected from the group consisting of tetrapropylammonium ion; tetraethylammonium ion; tripropylamine; triethylamine; triethanolamine; piperidine; cyclohexylamine; 2-methyl pyridine; N,N-dimethylbenzylamine; N,N-dimethylethanolamine; choline; N,N-dimethylpiperazine; 1,4-diazabicyclo-(2,2,2)octane; N-methyldiethanolamine; N-methylethanolamine; N-methylpiperidine; 3-methylpiperidine; N-methylcyclohexylamine; 3-methylpyridine; 4-methylpyridine; quinuclidine; N,N'-dimethyl-1,4-diazabicyclo(2,2,2)octane ion; tetramethylammonium ion; tetrabutylammonium ion; tetrapentylammonium ion; di-n-butylamine; neopentylamine; di-n-pentylamine; isopropylamine; t-butylamine; ethylenediamine; pyrrolidine; 2-imidazolidone; di-n-propylamine; and a polymeric quaternary ammonium salt $[(C_{14}H_{32}N_2)(OH)_2]_x$ wherein x is a value of at least 2.

23. Crystalline molecular sieve prepared by calcining the composition of claim 1 or claim 2 at a temperature sufficiently high to remove at least some of the organic templating agent present in the intracrystalline pore system.

24. The crystalline molecular sieves of claims 1 or 2 wherein the values of "w" and "z" have the following mole fraction values: "w" is $\geq 0.04$; and "z" is $\geq 0.03$.

25. The process of claim 13 wherein "b" has a value of from about 2 to about 500.

26. The process of claim 25 wherein "b" has a value of from about 2 to about 300.

* * * * *